United States Patent
Fukuoka et al.

(10) Patent No.: US 9,387,211 B2
(45) Date of Patent: Jul. 12, 2016

(54) METHODS FOR TREATMENT OF CUSHING'S DISEASE AND HYPERCORTISOLISM USING GEFITINIB

(75) Inventors: Hidenori Fukuoka, Culver City, CA (US); Shlomo Melmed, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 901 days.

(21) Appl. No.: 13/576,621

(22) PCT Filed: Jan. 31, 2011

(86) PCT No.: PCT/US2011/023247
§ 371 (c)(1),
(2), (4) Date: Aug. 1, 2012

(87) PCT Pub. No.: WO2011/094722
PCT Pub. Date: Aug. 4, 2011

(65) Prior Publication Data
US 2012/0301470 A1    Nov. 29, 2012

Related U.S. Application Data

(60) Provisional application No. 61/300,379, filed on Feb. 1, 2010.

(51) Int. Cl.
| | | |
|---|---|---|
| *A61K 31/5377* | (2006.01) | |
| *A61P 5/38* | (2006.01) | |
| *A61K 31/713* | (2006.01) | |
| *A61K 48/00* | (2006.01) | |
| *A61K 31/535* | (2006.01) | |
| *C12Q 1/48* | (2006.01) | |
| *G01N 33/74* | (2006.01) | |

(52) U.S. Cl.
CPC .............. *A61K 31/535* (2013.01); *C12Q 1/485* (2013.01); *G01N 33/74* (2013.01); *G01N 2500/10* (2013.01); *G01N 2800/048* (2013.01)

(58) Field of Classification Search
None
See application file for complete search history.

(56) References Cited

U.S. PATENT DOCUMENTS

| | | |
|---|---|---|
| 2005/0107386 A1 | 5/2005 | Narla et al. |
| 2008/0081802 A1 | 4/2008 | McConnell et al. |
| 2008/0248033 A1 | 10/2008 | Ferrara et al. |
| 2008/0268460 A1 | 10/2008 | Loganzo et al. |
| 2012/0308567 A1 | 12/2012 | Fukuoka et al. |

FOREIGN PATENT DOCUMENTS

| | | | |
|---|---|---|---|
| IN | WO 2006/090413 A1 * | 8/2006 | |
| WO | WO2011094716 | 8/2011 | |
| WO | WO2011094722 | 8/2011 | |

OTHER PUBLICATIONS

Endocrine Today [online]. Healio Nov. 2008. [retrieved on Jul. 27, 2015]. Retrieved from the Internet: <http://www.healio.com/endocrinology/adrenal/news/print/endocrine-today/%7B6224334e-508c-4b90-a1f1-d1d8ccd9e68d%7D/the-difficulties-of-cushings-syndrome>. pp. 1-8.*
ISR for PCT/US2011/023237.
IPRP for PCT/US2011/023237.
Written Opinion for PCT/US2011/023237.
Xia et al. Combining lapatinib (GW572016), a small moleule inhibitor of ErbB1 and ErbB2 tyrosine kinases, with therapeutic anti-ErbB2 antibodies enhances apoptosis of ErbB2—overexpressing breast cancer cells. Oncogene (2005). 24:6213-6221.
Vlotides et al. Cancer Research, vol. 68, p. 6377-6386, 2008.
Arora et al. The Journal of Pharmacology and Experimental Therapeutics, vol. 315, No. 3, p. 971-979, 2005.
IPRP for PCT/US2011/023247.
Written Opinion for PCT/US2011/023247.
ISR for PCT/US2011/023247.
Kirschner, Review: Emerging Treatment Strategies for Adrenocortical Carcinoma: A New Hope. The Journal of Clinical Endocrinology & Metabolism, 2006, vol. 9, No. 1, pp. 14-21; p. 14, left col., para 2; right col. para 1; p. 17, right col., para 2.
Broco et al. "Adrenocortical carcinoma—a diagnostic and therapeutic challenge" Publicao Trimestral vol. 17, No. 1, Jan. 2010. abstract, p. 60 section entitled "Clinical Practice" second paragraph; p. 65 second paragraph; (available online at <http://www.spmi.pt/revista/voll 7/eng_voll 7_n1_2010_59_88.pdf >).
Camahan et al. "Competitive Protein Tyrosine Kinase Fluorescence Polarization Immunoassays for High Throughput Screening Drug Discovery" Nov. 2001 (available online at < http://tools.invitrogen.com/downloads/L0664.pdf >).

* cited by examiner

*Primary Examiner* — Sharon Wen
(74) *Attorney, Agent, or Firm* — Nixon Peabody LLP; Hema Vakharia-Rao

(57) ABSTRACT

The invention relates to methods and kits for the treatment of, prevention of, and lowering the chances of developing Cushing's Disease and/or hypercortisolism by the administration of a tyrosine kinase inhibitor, such as gefitinib.

7 Claims, 18 Drawing Sheets

C.

D.

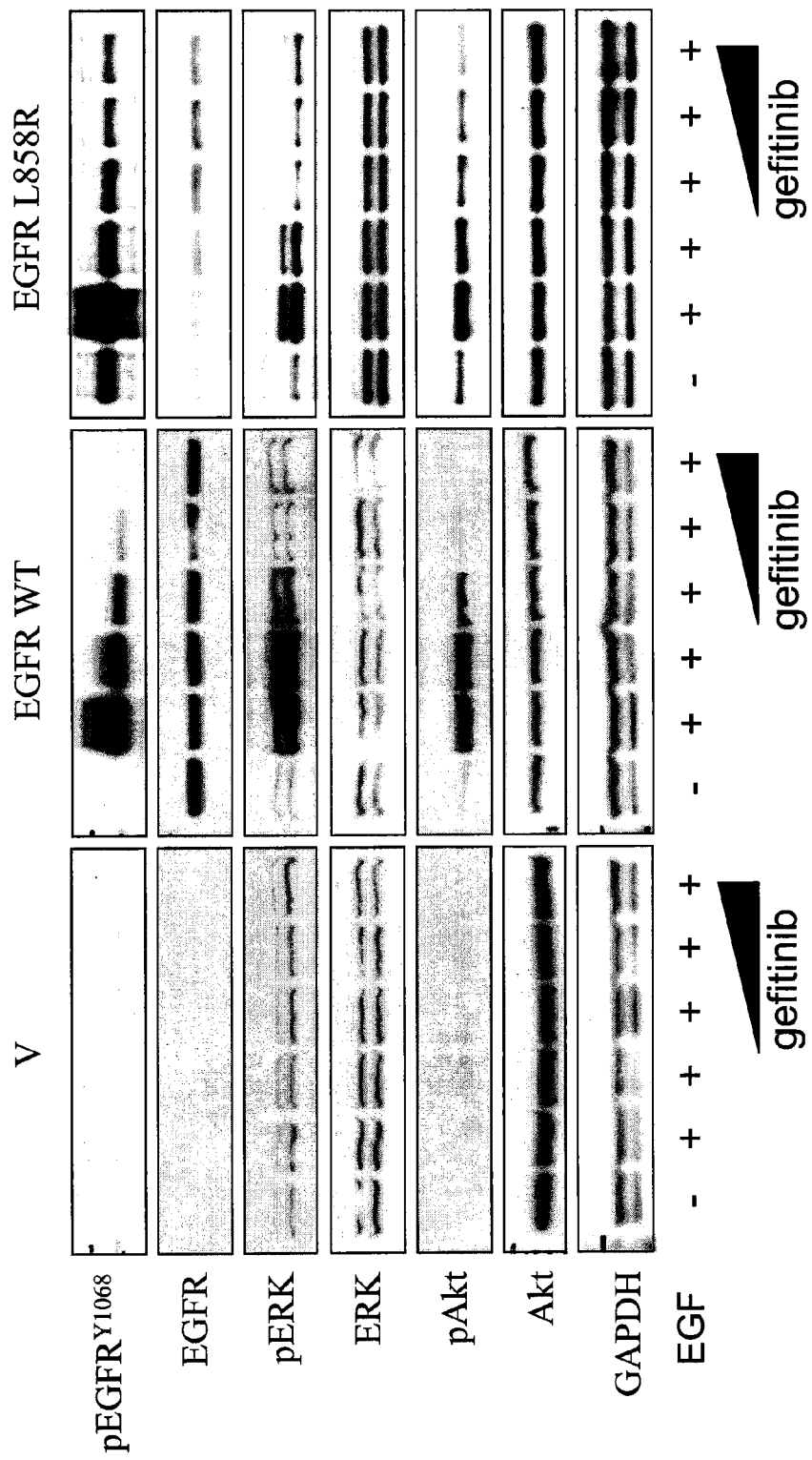

F.

G.

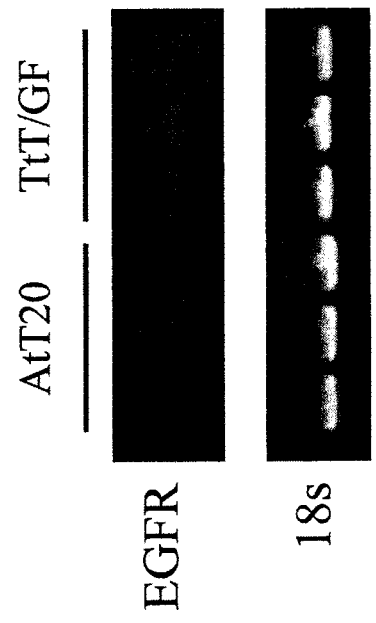

I.

E.

F.

D.

E.

F.

G.

METHODS FOR TREATMENT OF CUSHING'S DISEASE AND HYPERCORTISOLISM USING GEFITINIB

This application is the National Phase of International Application PCT/US11/23247, filed Jan. 31, 2011, which designated the U.S. and that International Application was published under PCT Article 21(2) in English. The present application also claims the benefit of the filing date of U.S. Provisional Application No. 61/300,379 filed Feb. 1, 2010, the contents of all which are incorporated herein by reference in their entirety.

The invention was made with government support under Grant No. CA07597 awarded by the National Institutes of Health. The government has certain rights in the invention.

FIELD OF INVENTION

This invention relates to treatment of Cushing's disease and hypercortisolism with tyrosine kinase inhibitors.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Pituitary tumors, accounting for ~15% of intracranial tumors, are invariably benign monoclonal adenomas and cause significant morbidity due to abnormal hormone secretion, and/or tumor mass effects compressing vital structures[1]. Adrenocorticotropic hormone(ACTH)-secreting tumors arising from pituitary corticotroph cells (Cushing's disease) exhibit poor prognosis, and cause hypercortisolemia resulting in osteoporosis, infections, psychiatric disorders, muscle atrophy, fat accumulation, hypertension, hyperglycemia and ultimately death[2-4].

Cushing's syndrome is a hormonal disorder caused by prolonged exposure of the body's tissues to high levels of the hormone cortisol. Sometimes called hypercortisolism, Cushing's syndrome is relatively rare and most commonly affects adults aged 20 to 50. People who are obese and have type 2 diabetes, along with poorly controlled blood glucose and high blood pressure, have an increased risk of developing the disorder. The abnormal exposure of the body to cortisol can result from a variety of physiological conditions and diseases. Treatment depends on the specific reason for excess cortisol and may include surgery, radiation, chemotherapy, or the use of cortisol-inhibiting drugs. If the cause is long-term use of glucocorticoid hormones to treat another disorder, the physician may gradually reduce the dosage to the lowest dose adequate for control of that disorder. Once control is established, the daily dose of glucocorticoid hormones may be doubled and given on alternate days to lessen side effects. In some cases, noncorticosteroid drugs can be prescribed.

No drug effectively targets ACTH-secreting pituitary adenomas. Current optimal treatment is surgical resection, with initial remission rates achieved by an expert pituitary surgeon ranging from 65-90% for microadenomas, and less than 65% for macroadenomas[2]. Post-operative recurrence rates for microadenomas are 10-20% at 10 years, and up to 45% for macroadenomas[2]. Surgery is further challenged by the fact that pre-operative pituitary tumor localization is often difficult even using high-resolution MRI, and inferior petrosal sinus sampling is often required for ACTH measurements to confirm the presence of a tumor[5-7]. Early results with the somatostatin analog pasireotide, or the dopamine agonist cabergoline have shown short-term biochemical remission in a minority of patients with Cushing's disease[8,9]. Long-term side effects and efficacy of these medications in patients with Cushing's disease are unknown, and pasireotide may predispose to hyperglycemia[10].

Epidermal growth factor (EGF) receptor activation, either as a result of a mutation, or due to ligand or receptor overexpression, is associated with a variety of human cancers[11]. EGF is also a mitogen for pituitary cells, and induces prolactin and ACTH synthesis[12]. Although pituitary tumors, including ACTH-secreting adenomas, express the EGF receptor[13-16], the role of the receptor in tumorigenesis remains unclear. In pituitary corticotroph tumors expressing the EGF receptor, $p27^{Kip1}$, a cyclin-dependent kinase inhibitor, was down-regulated[16]. Mice with disrupted p27 also develop pituitary tumors mostly expressing proopiomelanocortin (POMC), a precursor protein of ACTH[17-20]. Applicants therefore tested the function of EGF receptor (EGFR) signaling in ACTH-secreting pituitary adenomas, and hypothesized that the receptor could be a novel target for therapy of Cushing's disease.

Gefitinib (marketed as Iressa® by AstraZeneca and Teva), a tyrosine kinase inhibitor (TKI) targeting the EGFR, blocks activity at the ATP-binding site of the intracellular tyrosine kinase domain[21]. Gefitnib is a selective inhibitor of the epidermal growth factor receptor's (EGFR's) tyrosine kinase domain, and thus acts as an EGFR inhibitor. It is approved for the treatment of locally advanced or metastatic non-small cell lung cancer (NSCLC) in patients who have previously received chemotherapy. Gefitinib exhibits efficacy in treating pulmonary adenocarcinoma, especially in female Asian non-smokers. In these populations, a somatic mutation, either a deletion mutant of exon19 (del746_A750) or point mutation of exon21 (L858R) has been observed[22]. In other cancers which overexpress EGFR (either wild type or mutants), gefitinib has also been shown to be effective[23,24]. Here, Applicants show the functional role of EGFR in murine and canine corticotroph tumors and provide evidence supporting the use of gefitinib as a novel targeted therapy for Cushing's disease in subjects.

There is currently a need in the art for additional treatments for Cushing's Disease or hypercortisolism.

SUMMARY OF THE INVENTION

The invention provides methods for treating Cushing's Disease and/or hypercortisolism in a subject. The methods comprise providing a composition comprising a tyrosine kinase inhibitor and administering to the subject an effective amount of the composition, thereby treating Cushing's Disease and/or hypercortisolism in a subject.

The invention further provides methods for inhibiting and/or reducing Cushing's Disease and/or hypercortisolism in a subject. The methods comprise providing a composition comprising a tyrosine kinase inhibitor and administering to the subject an effective amount of the composition, thereby inhibiting and/or reducing Cushing's Disease and/or hypercortisolism in a subject.

Methods for promoting prophylaxis of Cushing's Disease and/or hypercortisolism are also provided herein. The methods comprise providing a composition comprising a tyrosine kinase inhibitor and administering to the subject an effective amount of the composition, thereby promoting prophylaxis of Cushing's Disease and/or hypercortisolism in a subject.

The invention also provides methods for screening for compounds that inhibit tyrosine kinase. The screening method comprises contacting the compound of interest with a cell expressing tyrosine kinase and assaying for amounts of ACTH. A reduction in the amount of ACTH compared to the control is indicative of the compound of interest inhibiting tyrosine kinase.

The invention further provides kits for treatment of Cushing's Disease and/or hypercortisolism, inhibition of Cushing's Disease and/or hypercortisolism, reduction of Cushing's Disease and/or hypercortisolism and/or promotion of prophylaxis of Cushing's Disease and/or hypercortisolism in a subject. The kit comprises a composition comprising a tyrosine kinase inhibitor and instructions for use of the composition for treatment of Cushing's Disease and/or hypercortisolism, inhibition of Cushing's Disease and/or hypercortisolism, reduction of Cushing's Disease and/or hypercortisolism and/or promotion of prophylaxis of Cushing's Disease and/or hypercortisolism in a subject.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
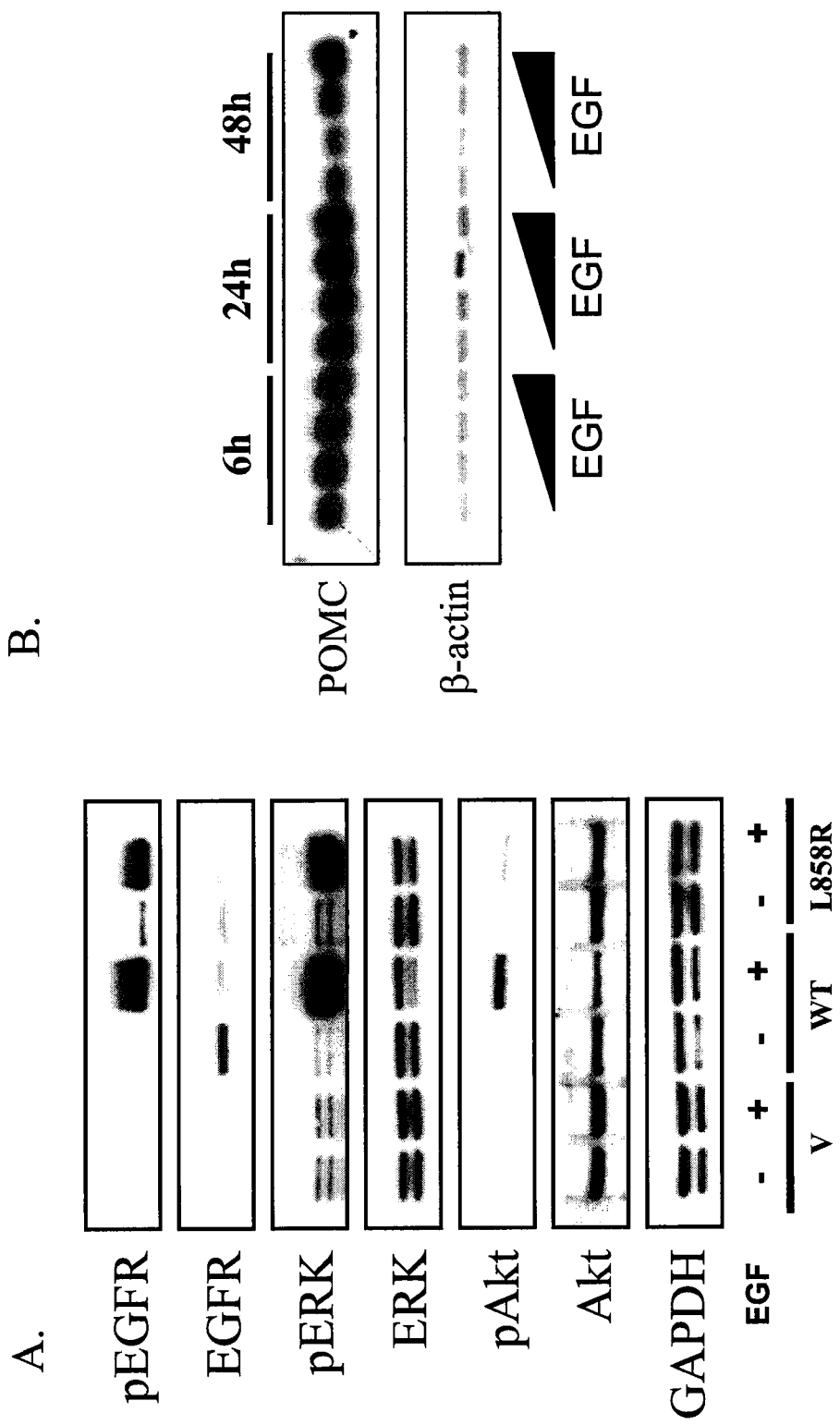
FIG. 1 shows that EGFR enhances pomc mRNA expression and ACTH secretion. A. AtT20 cells stably expressing wild type EGFR (EGFRWT), constitutively active EGFR (EGFRL858R) or empty vector (V), were treated with 5 nM EGF for 10 min, and Western blotting performed. B. EGFRWT were treated with EGF (0.5-50 nM) for the indicated times, and Northern blotting performed. C. EGFRWT, EGFRL858R, or V was transfected with Pomc promoter and pRL-TK for 24 hours. After 6 hours serum-deprivation, cells were stimulated with EGF (0.5-50 nM) for 24 hours. D. EGFRWT, EGFRL858R, or V were treated with 5 nM EGF for 24 hours. ACTH secretion in the culture medium was determined by RIA, and hormone secretion levels normalized for cell numbers. E. EGFRWT, EGFRL858R, or V were treated with gefitinib (0.01-10 µM) for 45 min prior to induction with 5 nM EGF for 10 min, and Western blotting performed. F. EGFRWT, EGFRL858R, or V were treated with gefitinib (0.1-10 µM) for 24 hours. ACTH secretion in the culture medium was determined by RIA and hormone secretion levels normalized for cell numbers. G. EGFRWT, EGFRL858R, or V were transfected with Pomc promoter and RSV-β-gal for 24 hours. After 6 hours serum-deprivation, cells were treated with gefitinib (0.1-10 nM) for 24 hours. Values are mean±SEM. * $p<0.05$ vs EGFRWT control, ** $p<0.01$ vs EGFRWT control, †$p<0.05$ vs EGFRL858R control, and ‡†$p<0.05$ vs EGFRL858R control. Representative results are from triplicate samples in at least two or more independent experiments. H. No endogenous EGFR present in AtT20 cells. I. Luciferase expression was induced by EGFR overexpression and further by EGF treatment. J. Gefitnib suppresses pomc promoter activity.
Figure 1:
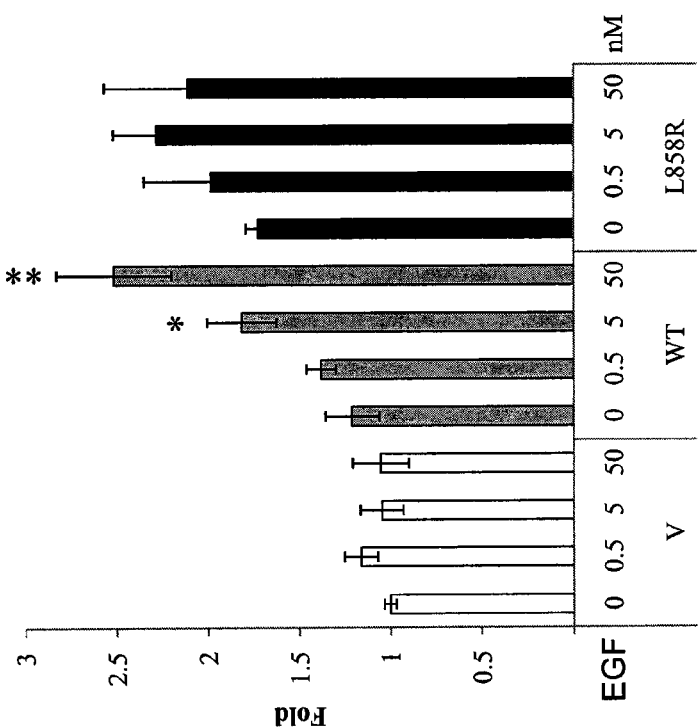
Figure 1:
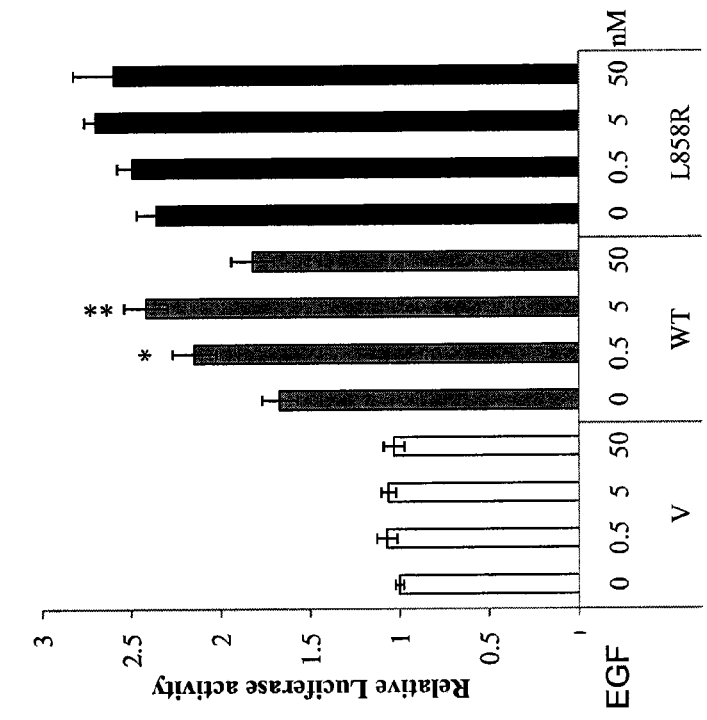
Figure 1:
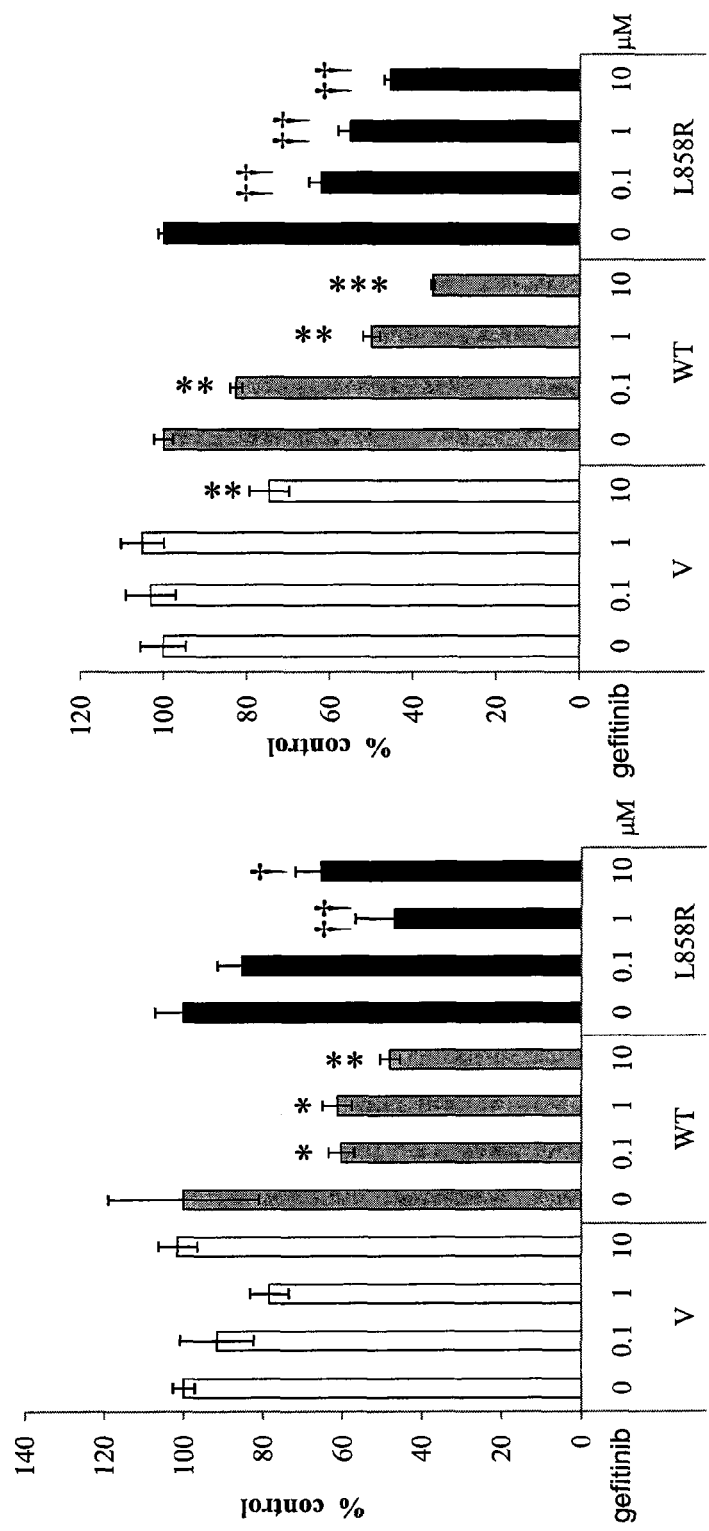
Figure 1:
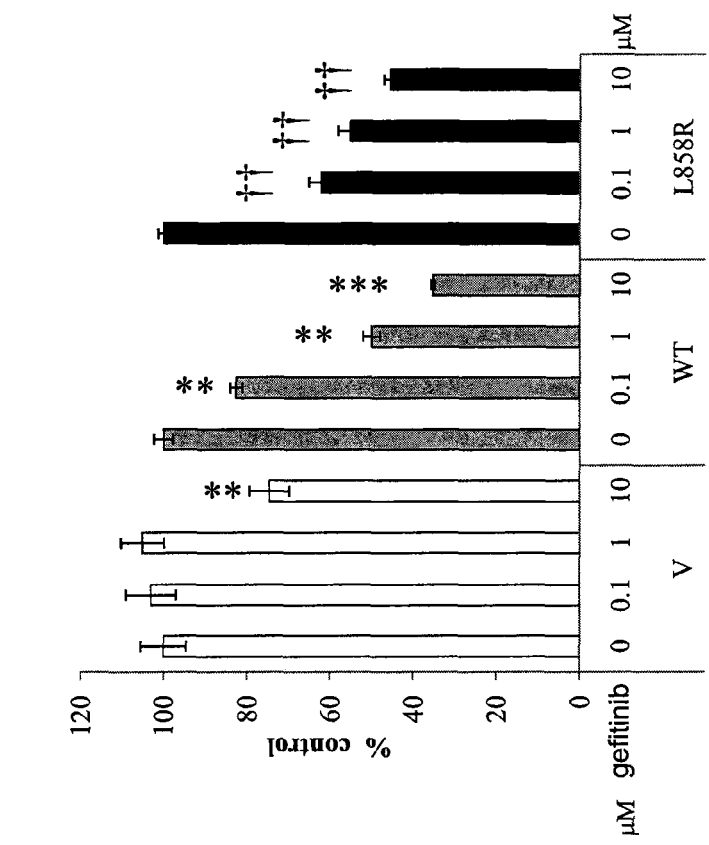
Figure 1:
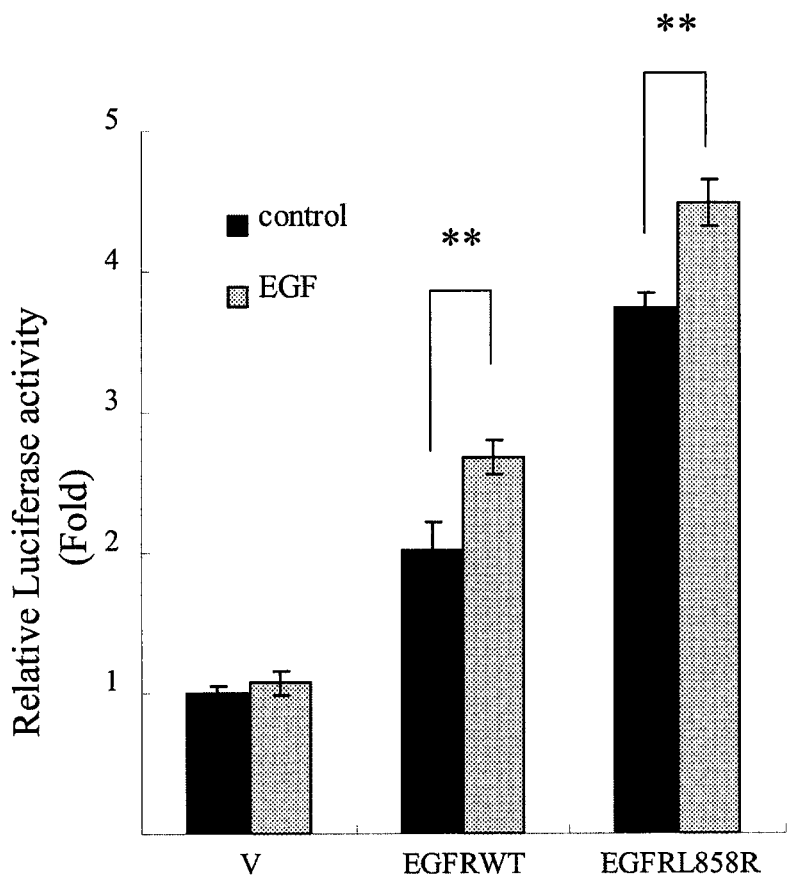
Figure 1:
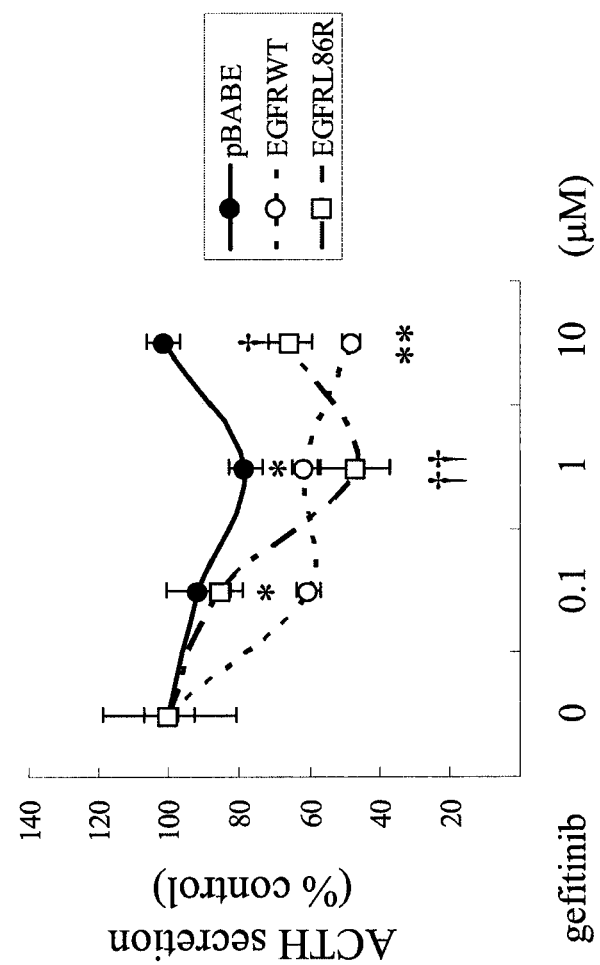

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced*

*Organic Chemistry Reactions, Mechanisms and Structure* 5th ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Conditions" and "disease conditions," as used herein may include, but are in no way limited to any form of Cushing's Disease or hypercortisolism.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Tyrosine kinase inhibitors," as used herein, refer to molecules and pharmaceuticals, the administration of which to a mammal result in the inhibition of tyrosine kinase—an enzyme that can transfer a phosphate group from ATP to a tyrosine residue in a protein. Examples of tyrosine kinase inhibitors include, but are not limited to, gefitinib (marketed as Iressa® by AstraZeneca and Teva), erlotinib hydrochloride (marketed as Tarceva® by Genentech and OSI Pharmaceuticals), lapatinib or lapatinib ditosylate (marketed as Tykerb® by GlaxoSmithKline), and pharmaceutical salts, equivalents and analogs thereof.

Therapeutic Methods of the Invention

The present invention describes methods and kits for using tyrosine kinase inhibitors, such as gefitnib, to treat conditions in a mammal, such as Cushing's Disease and hypercortisolism. While not wishing to be bound by any particular theory, the inventors believe that their findings that tyrosine kinase inhibitors, and gefitinib in particular, suppress ACTH cell and animal models of ACTH-secreting pituitary tumors, support the notion that administration of these compounds in a clinical setting may result in the treatment, prevention and/or lowering the chances of developing Cushing's Disease and/or hypercortisolism.

The present invention provides for a method of treating Cushing's Disease and/or hypercortisolism in a subject in need thereof, comprising: providing a quantity of a tyrosine kinase inhibitor and administering the quantity of the tyrosine kinase inhibitor to the subject to treat Cushing's Disease and/or hypercortisolism. In an embodiment, the tyrosine kinase inhibitor is gefitinib, a salt thereof, or a pharmaceutical equivalent thereof. In various embodiments of the invention, the subject has ACTH-secreting pituitary adenoma, such as Cushing's Disease and/or hypercortisolism.

The present invention also provides for a method of inhibiting Cushing's Disease and/or hypercortisolism in a subject in need thereof, comprising: providing a quantity of a tyrosine kinase inhibitor and administering the quantity of the tyrosine kinase inhibitor to the subject to inhibit Cushing's Disease and/or hypercortisolism. In an embodiment, the tyrosine kinase inhibitor is gefitinib, a salt thereof, or a pharmaceutical equivalent thereof. In various embodiments of the invention, the subject has ACTH-secreting pituitary adenoma, such as Cushing's Disease and/or hypercortisolism.

The present invention provides for a method of lowering a subject's chances of developing Cushing's Disease and/or hypercortisolism in a subject in need thereof, comprising providing a quantity of a tyrosine kinase inhibitor and administering the quantity of the tyrosine kinase inhibitor to the subject to lower the subject's chances of developing Cushing's Disease and/or hypercortisolism. In an embodiment, the tyrosine kinase inhibitor is gefitinib, a salt thereof, or a pharmaceutical equivalent thereof. In various embodiments of the invention, the subject has ACTH-secreting pituitary adenoma, such as Cushing's Disease and/or hypercortisolism.

The invention further provides methods for reducing the tumor size associated with Cushing's Disease and/or hypercortisolism in a subject in need thereof, comprising: providing a quantity of a tyrosine kinase inhibitor and administering the quantity of the tyrosine kinase inhibitor to the subject to reduce the tumor size associated with Cushing's Disease and/or hypercortisolism. In an embodiment, the tyrosine kinase inhibitor is gefitinib, a salt thereof, or a pharmaceutical equivalent thereof. In various embodiments of the invention, the subject has ACTH-secreting pituitary adenoma, such as Cushing's Disease and/or hypercortisolism.

The invention also provides methods for promoting prophylaxis of Cushing's Disease and/or hypercortisolism in a subject in need thereof, comprising: providing a quantity of a tyrosine kinase inhibitor and administering the quantity of the tyrosine kinase inhibitor to the subject to promote prophylaxis of Cushing's Disease and/or hypercortisolism. In an embodiment, the tyrosine kinase inhibitor is gefitinib, a salt thereof, or a pharmaceutical equivalent thereof. In various embodiments of the invention, the subject has ACTH-secreting pituitary adenoma, such as Cushing's Disease and/or hypercortisolism.

In other embodiments of the invention, the tyrosine kinase inhibitor is any one or more of a small molecule, a peptide, an antibody or a fragment thereof, a nucleic acid molecule, or a combination thereof. In an embodiment of the invention, the tyrosine kinase inhibitor is a small molecule. In one embodiment, the small molecule is gefitnib, a salt thereof, or a pharmaceutical equivalent thereof. In a further embodiment, the tyrosine kinase inhibitor is a nucleic acid molecule, wherein the nucleic acid molecule inhibits tyrosine kinase. For example, the nucleic acid molecule that inhibits tyrosine kinase may be an siRNA molecule of tyrosine kinase.

In a further embodiment of the invention, the tyrosine kinase inhibitor is an anti-tyrosine kinase antibody. In an embodiment, the antibody specifically binds tyrosine kinase so as to inhibit tyrosine kinase. The antibody may be any one or more of a monoclonal antibody or fragment thereof, a polyclonal antibody or a fragment thereof, a chimeric antibody, a humanized antibody, a human antibody or a single chain antibody. These antibodies can be from any source, e.g., rat, dog, cat, pig, horse, mouse or human. Fragments of antibodies may be any one or more of Fab, F(ab')2, Fv fragments or fusion proteins.

The subjects treated by the present invention include mammalian subjects, including, human, monkey, ape, dog, cat, cow, horse, goat, pig, rabbit, mouse and rat.

Various methods may be utilized to administer the composition of the claimed methods, including but not limited to aerosol, nasal, oral, transmucosal, transdermal, parenteral, implantable pump, continuous infusion, topical application, capsules and/or injections.

Dosages of the Invention

In some embodiments of the invention, the effective amounts of tyrosine kinase inhibitor in the composition can be in the range of about 10-50 mg/day, 50-100 mg/day, 100-150 mg/day, 150-200 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day or 2900-3000 mg/day. In one embodiment of the invention, the tyrosine kinase inhibitor is gefitinib.

In further embodiments of the invention, the effective amount of tyrosine kinase inhibitor for use with the claimed methods may be in the range of 10-50 mg/kg, 50-100 mg/kg, 100-150 mg/kg, 150-200 mg/kg, 100-200 mg/kg, 200-300 mg/kg, 300-400 mg/kg, 400-500 mg/kg, 500-600 mg/kg, 600-700 mg/kg, 700-800 mg/kg, 800-900 mg/kg, 900-1000 mg/kg, 1000-1100 mg/kg, 1100-1200 mg/kg, 1200-1300 mg/kg, 1300-1400 mg/kg, 1400-1500 mg/kg, 1500-1600 mg/kg, 1600-1700 mg/kg, 1700-1800 mg/kg, 1800-1900 mg/kg, 1900-2000 mg/kg, 2000-2100 mg/kg, 2100-2200 mg/kg, 2200-2300 mg/kg, 2300-2400 mg/kg, 2400-2500 mg/kg, 2500-2600 mg/kg, 2600-2700 mg/kg, 2700-2800 mg/kg, 2800-2900 mg/kg or 2900-3000 mg/kg. In one embodiment of the invention, the tyrosine kinase inhibitor is gefitinib Typical dosages of an effective amount of a tyrosine kinase inhibitor, such as gefitinib, can be in the ranges recommended by the manufacturer where known therapeutic compounds are used, and also as indicated to the skilled artisan by the in vitro responses or responses in animal models. For example, gefitinib is currently recommended at 250 mg orally, once daily, with or without food, for the treatment of NSCLC. The same or similar dosing can be used in accordance with various embodiments of the present invention, or an alternate dosage may be used in connection with alternate embodiments of the invention. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

Screening Methods of the Invention

Another aspect of the invention relates to assays and methods for identifying compounds that inhibit tyrosine kinase. In one embodiment, the method comprises contacting tyrosine kinase in a tyrosine kinase positive cell with the compound of interest and subsequently determining whether the contact results in altered amounts of ACTH. In an embodiment of the claimed methods, an alteration in the amount of ACTH is a decrease in the amount of ACTH. In one embodiment, a decrease in the amount of ACTH secretion is indicative that the molecule of interest is an inhibitor of tyrosine kinase. In another embodiment, decrease in the amount of ACTH synthesized is indicative that the molecule of interest is an inhibitor of tyrosine kinase. In a further embodiment, decrease in the amount of nucleic acid (for example, mRNA) encoding ACTH is indicative that the molecule of interest is an inhibitor of tyrosine kinase.

The compound of interest that inhibits tyrosine kinase may be any one or more of a small molecule, a peptide, an antibody or a fragment thereof and a nucleic acid molecule.

Assays that may be employed to identify compounds that inhibit tyrosine kinase include but are not limited to microarray assay, quantitative PCR, Northern blot assay, Southern blot assay, Western blot assay immunohistochemical assays, binding assays, gel retardation assays or assays using yeast two-hybrid systems. A person skilled in the art can readily employ numerous techniques known in the art to determine whether a particular agent inhibits tyrosine kinase.

Pharmaceutical Compositions

In various embodiments, the present invention provides pharmaceutical compositions including a pharmaceutically acceptable excipient along with a therapeutically effective amount of a tyrosine kinase inhibitor, such as Gefitnib. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Kits of the Invention

The present invention is also directed to kits to treat Cushing's Disease and hypercortisolism. The kit is an assemblage of materials or components, including at least one of the inventive compositions. Thus, in some embodiments the kit contains a composition including a tyrosine kinase inhibitor, such as gefitnib, as described above.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat or prevent Cushing's Disease and/or hypercortisolism in a subject. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a bottle used to contain suitable quantities of an inventive composition containing a tyrosine kinase inhibitor, such as gefitnib. The packaging material generally has an external label which indicates the contents and/or purpose of the kit and/or its components.

EXAMPLES

The following example is provided to better illustrate the claimed invention and is not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Experimental Methods

Materials

DMEM, and penicillin/streptomycin were purchased from Invitrogen. EGF was from Sigma. Gefitinib (Iressa) was purchased from Biaffin GmbH & Co.

Plasmids

The various deletion mutant of rat POMC promoter containing, −379/+63, −323/+63, −200/+63, −155/+63, −100/+63, −34/+63, were cloned by PCR from previously described reporter plasmid[30] using following primers:

5'-CGAGTCGACGATCTTGATTTCACAAGACTCCATAC-3' for -480 forward (F),

5'-CGTGTCGACGGCAGATGGACGCACACAGG-3' for -379 F,

5'-AGAGTCGACCCTGCCTCACACCAGGATG-3' for -379 F,

5'-GTGGTCGACCCAGCCTCCGCACTTTCC-3' for -200 F,

5'-CGCGTCGACGACCGGGAAGCCCCCC-3' for -155 F,

5'-GCCGTCGACTCGCTTGTTGCGTTGCAGAAG-3' for -100 F,

5'-CAAGTCGACAGGTATAAAAGAAGAGAGAAGAGTGAC-3' for -34 F,

5'-CAGGGATCCTGTTCAGTGGCCTCTCTTAGTC-3' for +63 reverse, and digested with Sal1 and BamH1, then sub-cloned into pGL4.10 vector (Promega) which digested with Xho1 and Bg1α. All constructs were verified by sequencing.

Stable Transfected Cells

AtT20 murine corticotroph tumor cells secreting ACTH were purchased from the American Type Culture Collection. V, EGFRWT or EGFRL858R cells were generated by a retroviral infection which containing the wild type EGFR cDNA, constitutively active form (L858R) of EGFR cDNA, or empty vector (pBABEpuro) purchased from Addgene (Addgene plasmid 11011 and 11012). Stable colonies were selected in the presence of 100 ng/ml puromycin (Sigma). A vector control cell line pBABEpuro was simultaneously established by transfecting pBABEpuro that lacked inserted cDNA. After selection and propagation of stable transfectants, cells were cultured in DMEM medium containing 10% FBS, penicillin/streptomycin, and 100 ng/m puromycin. After synchronization by serum starvation (medium containing 1% FBS for ~16 h), cells with treatment agents was grown in fresh serum-depleted medium (1% FBS), and samples collected at the indicated times.

Northern Blotting

Probes for murine POMC was generated as described[47]. The β-actin probe was a 1.076 kb fragment of the mouse β-actin gene (Ambion). RNA extraction was performed using Trizol reagent (Invitrogen) according to the manufacturer's instructions. For Northern blot analysis, 10-20 μg of total RNA was electrophoresed on a 1% agarose, 6.4% formaldehyde gel, transferred to a Hybond-N+ membrane (Amersham) and UV cross-linked. Probes were labeled with (α-32P)CTP using the Prime-it random primer labeling kit (Stratagene). Micro Bio-Spin chromatography columns (Bio-Rad) were used to purify probes. Membrane prehybridization and hybridization were performed using QuickHyb Solution (Stratagene) and then exposed to Hyperfilm MP (Amersham) for 1 to 4 days at −70° C.

Real-Time RT-PCR

Total RNA was extracted with Trizol reagent (Invitrogen) according to instructions of the manufacturer. The amount and the integrity of RNA were assessed by measurement of absorbance at 260 and 280 nm. Total RNA was reverse-transcribed into first-strand cDNA using iScript cDNA synthesis kit (Bio-Rad Laboratories, Inc.) according to the manufacturer. Quantitative PCR reactions were carried out in the iQ5 Multicolor Real-time PCR Detection System (Bio-Rad Laboratories, Inc.) as described[28]. Certified $RT^2$ primer assays for mouse pomc, were purchased from SuperArray. Primer sequences (Invitrogen) were following 5'-GGA-CATCTAAGGGCATCACA-3' (18s rRNA forward (F)), 5'-TCAAGAACGA-AAGTCGGAGG-3' (18s rRNA reverse (R)), 5'-GGCCTCTGTGGAAGTGAGTG-3' (canine pomc F), 5'-ACGCCAGCAGGTTACTTTCC-3' (canine pomc R), 5'-CCTCC-TGCCGTATTACCCTTG3' (canine GUS F), 5'-TCTGGACGAAGTAACCCTTGG-3' (canine GUS R), 5'-TCACTGGTGAGAACCCCCT-3' (canine RPS5 F), 5'-CCTGATT-CACACGGCGTAG-3' (canine RPS5R).

TaqMan PCR

TaqMan Gene Expression Assays for canine EGFR (cEGFR cf02626541_m1) were purchased from Applied Biosystems (Foster City, Calif.). Amplicons were detected using the relevant probes tagged with MGB quencher and FAM dye. TaqMan canine β-actin control Expression Assays with probe tagged with MGB and VIC (Applied Biosystems) were used as reference gene. Real-time PCR was carried out in a MicoAmp Optical 96-well plate in ABI Prism 7700 Sequence Detector (Applied Biosystems) as described previously[48]. Tested sample signals were normalized to parallel values obtained for β-actin.

Western Blotting

After the completion of treatments, the cells were placed on ice and washed with cold PBS. For protein extraction, cells were lysed in 100 μl of RIPA buffer (Sigma) containing complete protease inhibitor cocktail tablets (Roche Molecular Biochemicals) and phosphatase inhibitor cocktail 2 (Sigma). Lysates were centrifuged at 13,000×g for 10 min at 4° C. and protein concentrations determined by BCA protein assay reagent (Thermo Scientific). Western blot analysis was performed according to the guidelines of NuPAGE electrophoresis system protocol (Invitrogen). In brief, whole cell lysates (~50 μg protein per lane) were heated for 5 min at 100° C., respectively. Proteins were separated on 4 to 12% NuPAGE Bis-Tris gels and electrotransferred for 1 h to polyvinylidene difluoride (Invitrogen). Membranes were blocked for 1 h in 5% nonfat dry milk or 5% bovine serum albumin in TBS-T buffer, and incubated overnight with primary antibody. The following primary antibodies were used: anti-pErk1/2, anti-Erk1/2, anti-Akt, anti-pEGFR (Tyr1068), anti-EGFR, anti-caspase3, and anti-pRb (Ser780) from Cell Signaling Technology, anti-p53, anti-p27, anti-Rb, anti-E2F1 and anti-GAPDH from Santa Cruz Biotechnology, and anti-pAkt (Ser473), and anti-pttg from Abcam. After washing with TBS-T, membranes were incubated with peroxidase-conjugated secondary antibody for 1 h (5% nonfat dry milk or 5% bovine serum albumin in TBS-T buffer). Blots were washed and hybridization signals measured by enhanced chemiluminescence detection system (Amersham).

Soft Agarose Colony-Forming Assay

Base layers consisting of growth medium containing 0.6% low-melting point agarose (Invitrogen) were poured onto 6-well plates and allowed solidify. Cells ($8 \times 10^3$ per well) were plated in triplicate in top layers consisting of growth medium containing 0.3% agarose. 7-10 days later, cells were stained with 0.2% iodonitrotetrazolium chloride (Invitrogen), and colonies composed of ≥50 cells were counted manually in 5 randomly selected fields.

Cell Proliferation Assay

EGFR WT cells were plated at a density of $2 \times 10^4$ per well in 12-well plates with growth medium. Cells were counted by hemocytometer at the indicated times.

BrdU Incorporation

BrdU incorporation was measured by 5-Bromo-2'-deoxyuridine Labeling and Detection Kit II from Roche (Cat. No. 11 299 964 001). Cells were plated at a density of $8 \times 10^5$ cells per 10 cm-dish in serum supplemented media and allowed to attach. Cells were starved for overnight in 1% FBS media, treated with gefitinib for 24 hours, and incubated in media containing 10 μM BrdU for one hour. Fixative was prepared by adding 30 mL of 50 mM glycin solution (pH 2.0) to 70 mL ethanol. Cells were fixed for overnight at −20° C. Cells were washed with PBS, and resuspended in incubation solution with anti-BrdU antibody (1:10) for 30 minutes at 37° C. with gentle agitation. Cells were washed with PBS, and resuspended in 100 ul of 1% BSA/PBS with anti-mouse Alexa 488 secondary antibody (1:250) and incubated for 1.5 hours in the dark. Samples were washed with PBS and fluorescence was measured by flow cytometry.

TUNEL Assay

Cells were plated at a density of $5 \times 10^4$ cells per well in serum supplemented media and allowed to attach on poly-D-Lysine coated glass slides in 12-well plate. Cells were starved for overnight in DMEM with 1% FBS, and treated with gefitinib for 24 hours. Cells were fixed for 2 hours by 4% paraformaldehyde in PBS and permeabilized for 15 minutes by 0.1% TritonX-100 in 0.1% sodium citrate. 100 μl of label solution/enzyme solution mixture were added to cells and incubated at 37° C. for 1 hour. Washed samples were mounted on microscope slides and observed under confocal microscope.

Hormone Assay

RIAs for mouse ACTH were performed in duplicate, using reagents provided by the National Hormone and Pituitary Program, National Institute of Diabetes and Digestive and Kidney Diseases (Harbor-UCLA Medical Center, Torrance, Calif., USA). Iodination of ACTH (5 μg) with iodine-125 (500 μCi) (PerkinElmer life & Analytical Sciences, Boston, Mass., USA) mixed with 0.1 mg Iodo-Gen (Pierce, Rockford, Ill.) was performed using 10-ml columns prepared by G-75 Sephadex (Sigma Chemical Co.). Low interspecies cross-reactivity of the ACTH assays were previously shown[49].

Cultures of Canine ACTH Producing Pituitary Tumor-Derived Cells

After washing with medium, tumor tissues were chopped with a sterile scalpel into approximately 1-2 mm pieces. Tissues were rinsed and digested with DMEM containing 0.3% BSA, 0.35% collagenase, and 0.15% hyaluronidase at 37° C. for 30 min. The mixture was centrifuged at 1,500 rpm for 5 min at 4° C., and the cell pellet resuspended in an appropriate volume of culture medium containing 10% FBS and antibiotics in 48 well plates. After 24 hr incubation with serum depleted starvation medium (DMEM with 0.3% BSA), treatment agents were added with fresh serum-depleted medium (0.3% BSA), and medium collected for RIA. RNA was extracted after 24 hr treatment. Medium was also collected at baseline. To normalize for cell number effect, the PRL value of treated medium was divided by that of pre-treatment starvation medium to obtain a treated value for each well (n=4).

Immunofluorescence

Tumor specimens were fixed in 10% formalin and embedded in paraffin. After deparaffinization, and antigen retrieval, slides were blocked in 10% goat serum in 1% bovine serum albumin-PBS and then incubated overnight with primary antibody at 4° C. The following antibodies were used: rabbit polyclonal anti-EGFR (ab2430; 1:50; abcam), mouse monoclonal anti-ACTH (02A3; 1:50; Dako), and rabbit polyclonal anti-Tpit (1:200; kindly provided by Dr. Jacques Drouin, Montreal, Canada). Following washes, slides were incubated with Alexa Fluor goat anti-rabbit 488 (H+L) or anti-mouse 568 (H+L) secondary antibodies (1:500; Invitrogen) for 2 h at room temperature, and following such, slides were mounted with Prolong Gold antifade reagent with DAPI (Invitrogen). For co-staining, ACTH was detected using Alexa 568 conjugated anti-mouse secondary antibody and Tpit or EGFR staining detected with Alexa 488 conjugated anti-rabbit secondary antibody. Confocal microscope images were obtained using TCS-SP confocal scanner (Leica Microsystems) in a dual-emission mode to separate autofluorescence from specific staining.

Animals

In accordance with Institutional Animal Care and Use Committee of Cedars-Sinai Medical Center guidelines, 6- to 8-wk-old female Nu/J (Harlan Sprague Dawley, Inc.) were inoculated with V or EGFRWT stable transfectants ($1\times10^6$ cells/group). Mice were fed with a commercial pelleted diet ad libitum and tap water. Tumor volumes were measured with a caliper and calculated using the formula, $\pi/6 \times$ large diameter$\times$small diameter$^2$ as previously described[28]. Three days after inoculation, mice with V or EGFRWT were divided into two groups respectively (n=10/group) and treated with gefitinib (100 mg/kg), or vehicle (0.5% methylcellulose, 0.5% tween80/PBS; 100 µl) via oral gavage daily for 10 days. On the last treatment day (day 10), mice were euthanized using $CO_2$ inhalation followed by decapitation. Cardiac blood was collected with 18-gauge syringes and tumors excised and weighed.

Statistical Analysis

Results are expressed as mean±SEM. Differences were assessed by one-way ANOVA following Scheffe's F test. $P<0.05$ was considered significant.

Example 2

As ACTH-secreting tumors express the EGFR family, the inventors tested EGFR signaling in murine corticotroph tumor cell regulation as a potential target for drug therapy of Cushing's tumors. They generated stable EGFR AtT20 corticotroph cell transfectants using retroviral (Addgene plasmid 11011, 11012) infection, and tested intracellular signal transduction, pomc gene expression, and ACTH secretion. The inventors inoculated stable EGFR overexpressing hormone-secreting cells to Nu/J mice, and treated them with oral gefitinib, an EGFR tyrosine kinase inhibitor. The inventors also treated primary cultured pituitary cells derived from resected canine ACTH secreting adenomas with gefitinib.

After selection and propagation, pomc gene expression was enhanced by EGF treatment (~1.7 fold, p<0.01) in stable EGFR AtT20 transfectants (EGFR-AtT20), while empty vector transfectants (EV-AtT20) did not respond to EGF. ACTH secretion was induced (~1.7 fold, p<0.01) in EGFR-AtT20 transfectants. EGF induction of phospho-STAT3 was dose dependently attenuated by gefitinib (0.01-10 µM). Furthermore, dominant negative STAT3 overexpression also attenuated pomc promoter induction by EGF. Treatment with gefitinib (0.1-10 µM) dose dependently suppressed both ACTH secretion (~50%, p<0.01), and pomc promoter activity (~30%, p<0.01). Gefitinib also induced apoptosis with enhancing cleaved-caspase 3 levels. BrdU incorporation was suppressed by gefitinib (~60%, p<0.01). Tumors in Nu/J mice inoculated with EGFR-AtT20 transfectants were larger than those injected with EV-AtT20 (76±4 vs 45±6 mg, p<0.05). EGFR-AtT20 implanted mice treated with gefitinib (100 mg/kg) exhibited decreased tumor size (~40%, p<0.01) and decreased serum ACTH levels (640±17 vs 378±83 ng/ml, p<0.05). Elevated plasma glucose levels in these hypercortisolemic mice were suppressed by gefitinib in mice with EGFR-AtT20 transfectants (392±9 vs 351±14 mg/dl, p<0.05). Next, the inventors treated 5 primary canine corticotroph tumor cell cultures with gefitinib. In 4 of 5 tumors, gefitinib dose-dependently suppressed ACTH levels (−50%, p<0.01), and pomc expression levels (−70%, p<0.01).

As corticotroph EGFR signaling induced ACTH expression and secretion via STAT3, and gefitinib blocked corticotroph growth and function in vitro and in vivo, the inventors believe that inhibition of this receptor may effectuate a targeted therapy for Cushing's Disease.

Example 3

Effects of EGF and Gefitinib on Pomc Expression and ACTH Secretion

Since AtT20 murine corticotroph pituitary tumor cells (AtT20) do not express endogenous EGFR (FIG. 1H), we generated stably transfected AtT20 cells using a retroviral vector containing wild type EGFR cDNA (EGFRWT), a constitutively active form (L858R) of EGFR cDNA (EGFRL858R), or empty vector (V). Western blot results showed abundant EGFR protein expression in stable but not in V transfectants (FIG. 1A). EGFRL858R exhibited tyrosine auto-phosphorylation even without added ligand to the medium, and EGF treatment induced phosphorylation of the receptor both in EGFRWT and L858R transfectants (FIG. 1A). MAPK and Akt pathways were activated by EGF in both EGFR transfectants, and the effects of added ligand were more pronounced in EGFRWT than in L858R. Northern blotting showed that EGF dose dependently enhanced pomc expression levels in EGFRWT (~2 fold, p<0.05, FIG. 1B). Next, we tested transcriptional activity to determine whether EGF directly regulates the pomc promoter. Luciferase expression was induced by EGFR overexpression itself (L858R: ~2.5 fold>WT: ~1.7 fold>V) and further enhanced by EGF treatment in EGFRWT (~1.5 fold, p<0.01), but not in EGFRL858R transfectants (FIGS. 1C, 1I). ACTH secretion in the culture media was enhanced by EGFRL858R overexpression itself (~1.7 fold, p<0.001) but not in EGFRWT, while EGF dose dependently further induced ACTH levels only in EGFRWT transfectants (~2.5 fold, p<0.01, FIG. 1D). Next, we tested whether blocking EGFR activity would suppress hormone expression and secretion. First, we confirmed the blocking effects of gefitinib, a TKI for EGFR, on EGFR downstream signalling. Western blotting analysis showed that gefitinib dose dependently suppressed EGF-induced phosphorylation of EGFR, ERK and Akt both in EGFRWT and in L858R, but not in V transfectants (FIG. 1E). Radioimmunoassay (RIA) and luciferase assay results showed that gefitinib attenuated ACTH secretion (~60%, p<0.01 both in EGFRWT and L858R), and pomc promoter activity (~63%, p<0.001 in EGFRWT, ~58%, p<0.01 in EGFRL858R), while the highest gefitinib dose (10 μM) suppressed pomc promoter activity even in control cells (~23%, p<0.01 FIGS. 1F, G, J).

Example 4

EGF Induces Pomc Promoter Activity Via PitxRE

Figure 2:
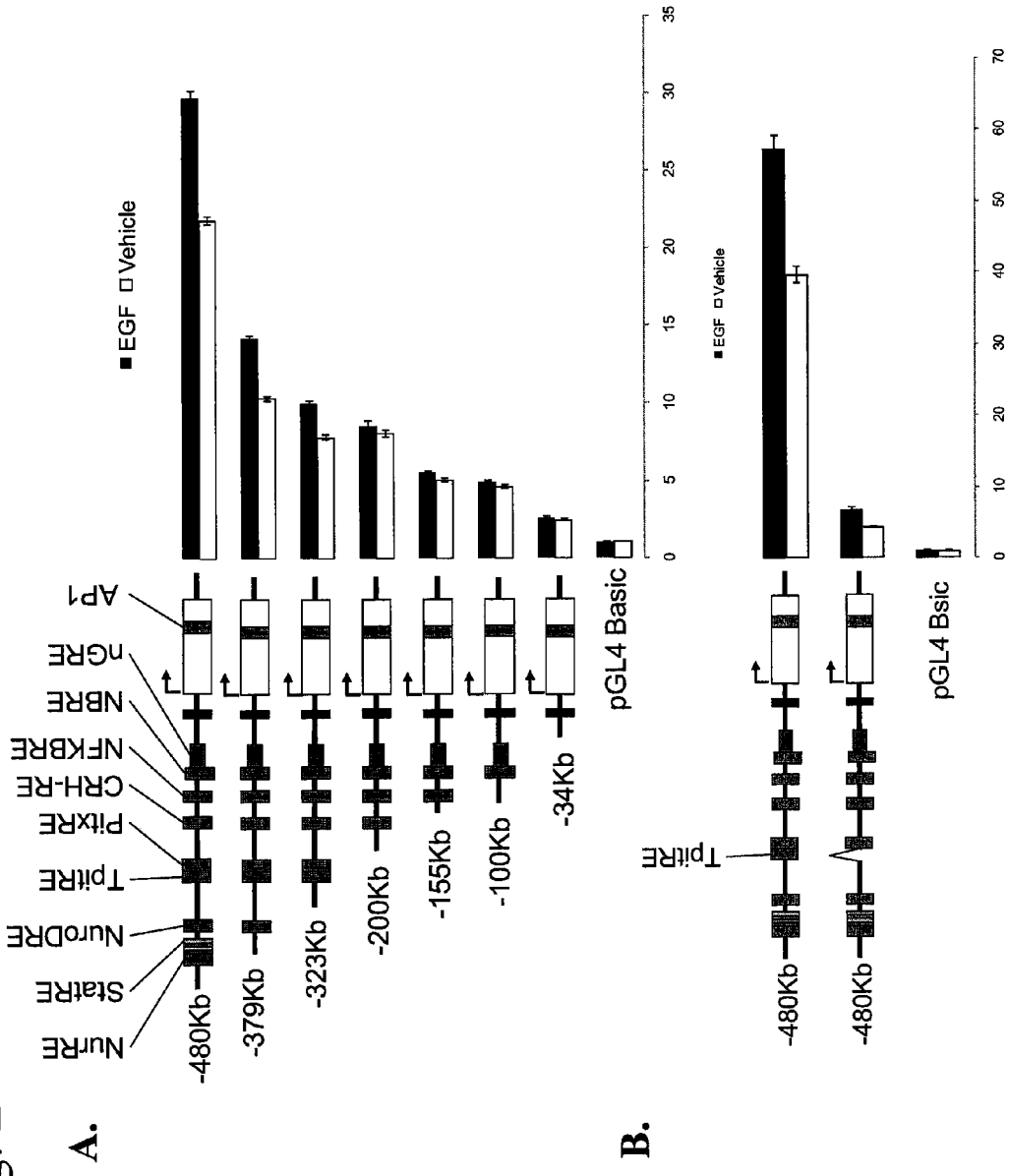
FIG. 2 shows that EGF enhances pomc promoter activity via Pitx1RE. A. EGFRWT was transfected with truncated mutants of the Pomc promoter and pRL-TK for 24 hours. After 6 hours serum-deprivation, cells were stimulated with 5 nM EGF for 24 hours. B. EGFRWT was transfected with TpitRE deletion mutants of the Pomc promoter and pRL-TK for 24 hours. After 6 hours serum-deprivation, cells were stimulated with 5 nM EGF for 24 hours. Values are mean±SEM. * $p<0.05$, ** $p<0.01$. Representative results are from triplicate samples in at least two or more independent experiments.
Figure 2:
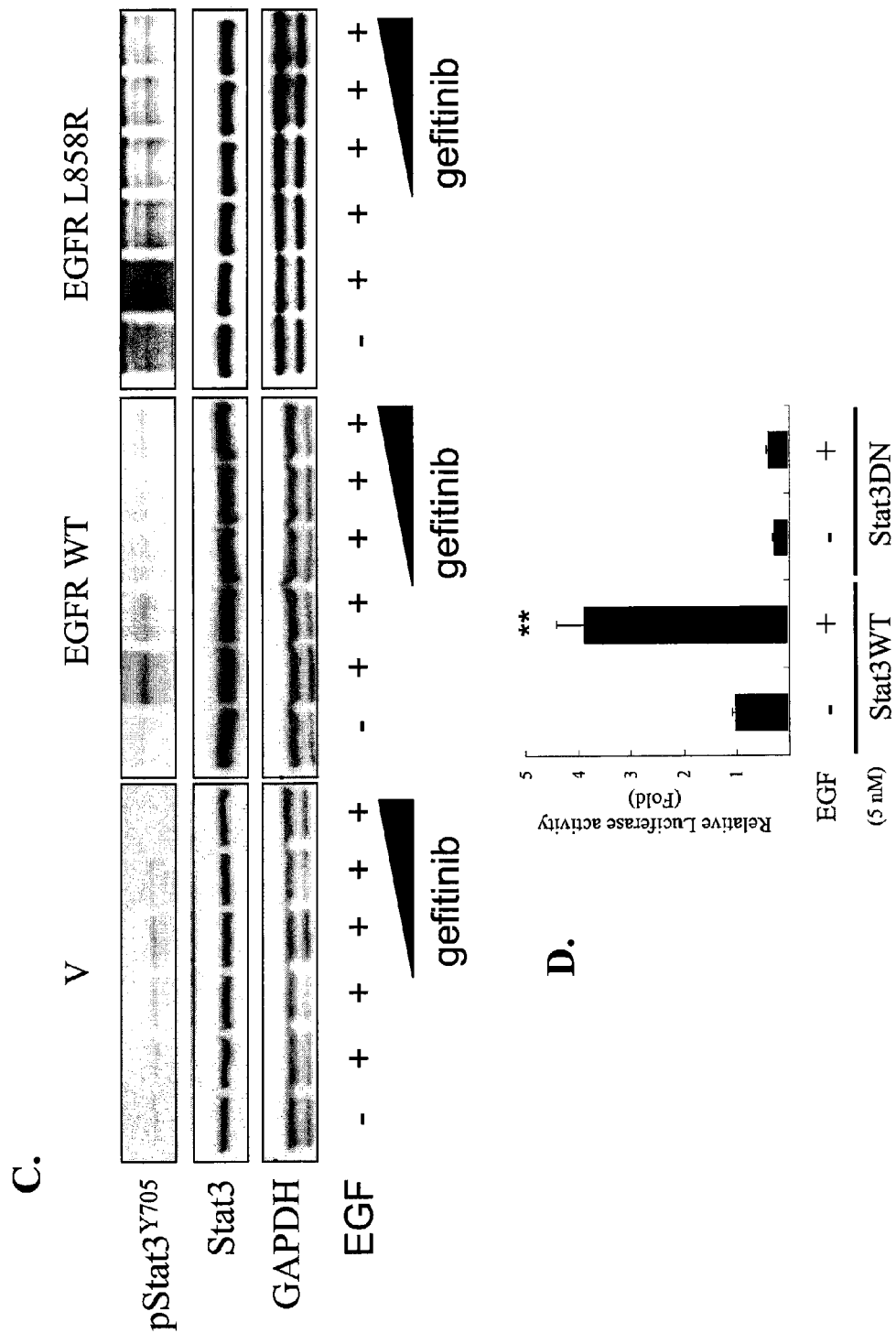

To determine the regulatory elements of the pomc promoter required for EGF signalling, we generated truncated mutants of the pomc promoter with pGL4 Basic luciferase expression vector. Treatment with EGF in EGFRWT transfectants, showed that deletion of Tpit and Pitx1 responsive elements (RE) prevented EGF induction of pomc promoter activity (FIG. 2A). Next we generated selective TpitRE deletion mutants of the pomc promoter which responded to EGF, suggesting that TpitRE is not required for EGF signalling to pomc (FIG. 2B).

Example 5

Figure 3:
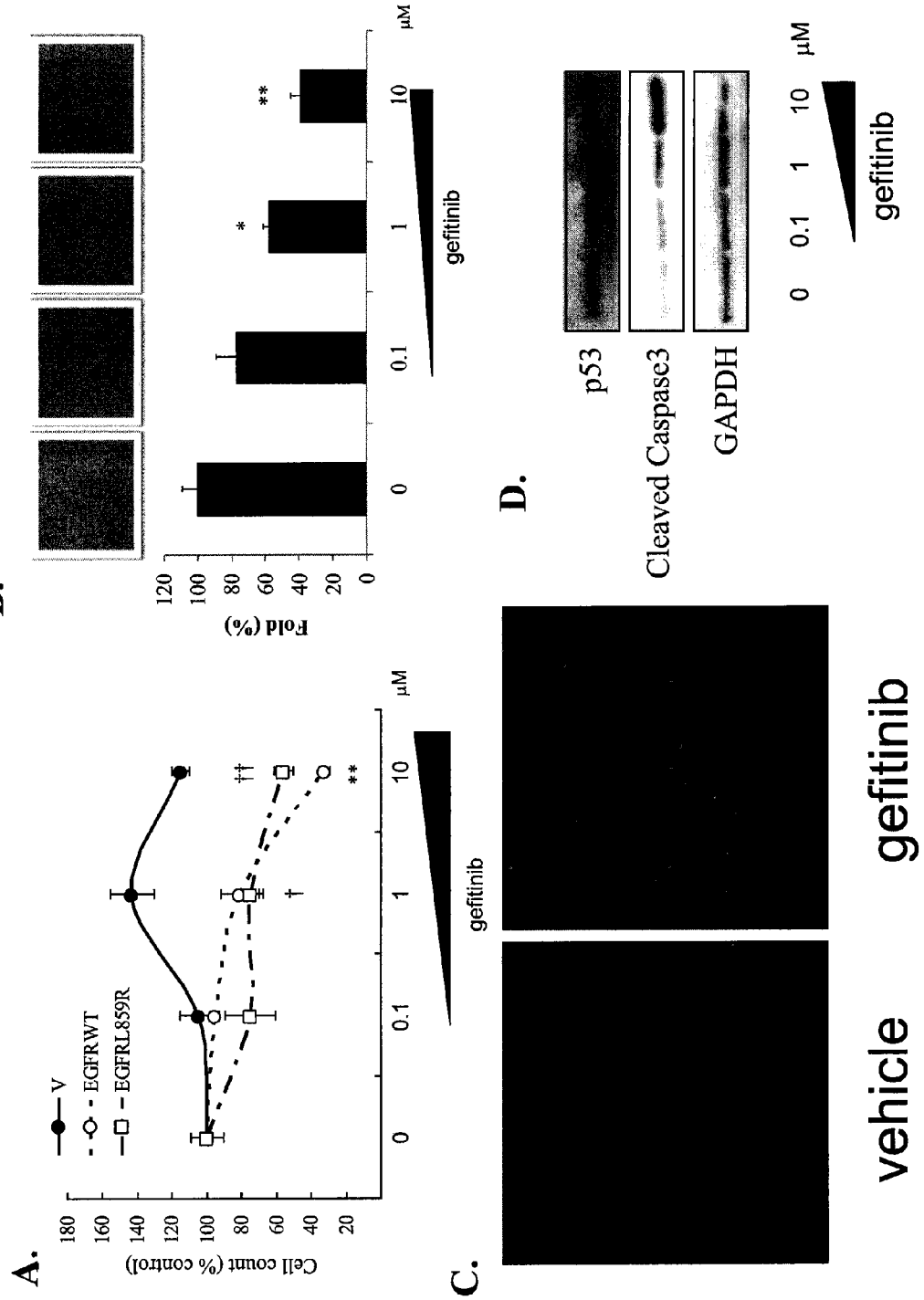
FIG. 3 shows the effects of gefitinib on corticotroph adenoma cell proliferation. A. EGFRWT, EGFRL858R, or V were treated with gefitinib (0.1-10 µM) for 24 hours, and cells counted. B. EGFRWT cells were seeded (4,000 per well) for colony-forming assay, and gefitinib (0.1-10 µM) added with serum-depleted media every third day. Colonies were counted from five randomly selected fields. C. EGFRWT, was treated with gefitinib (0.1-10 µM) for 48 hours, and TUNEL staining performed. D. EGFRWT, was treated with gefitinib (0.1-10 µM) for 48 hours, and Western blotting performed. E. EGFRWT, EGFRL858R, or V were treated with gefitinib (0.1-10 µM) for 24 hours, BrdU staining performed and incorporation quantified using flow cytometry. F. EGFRWT was treated with gefitinib (0.1-10 µM) for 24 hours, and Western blotting performed. Values are mean±SEM. ** $p<0.01$ vs V control, †$p<0.05$ vs EGFRWT control ††$p<0.01$ vs EGFRWT control, ‡$p<0.05$ vs EGFRL858R control ‡‡$p<0.01$ vs EGFRL858R control. Representative results are from triplicate samples in at least two or more independent experiments.
Figure 3:
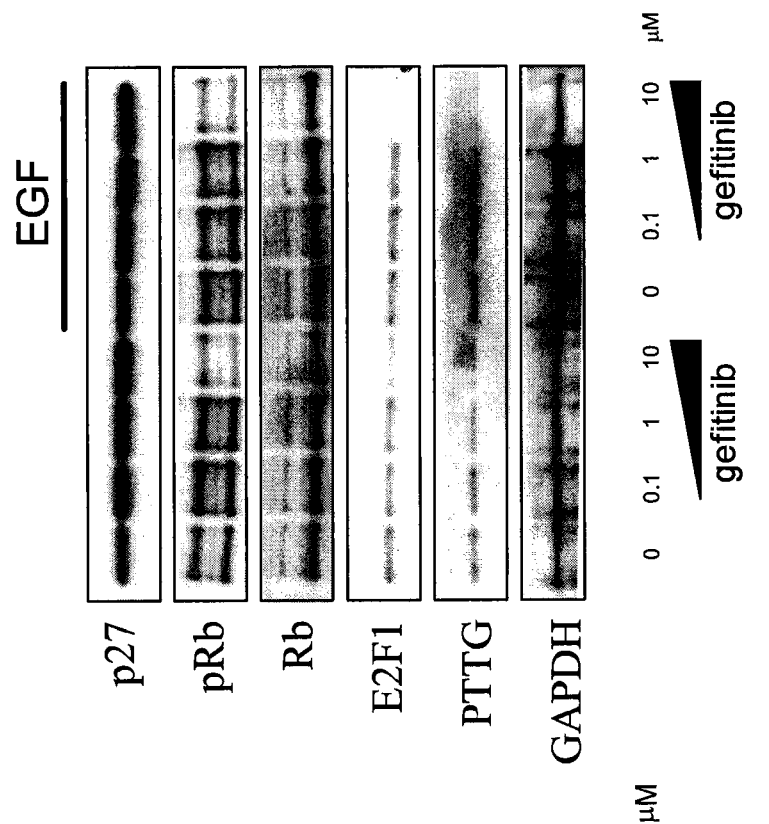
Figure 3:
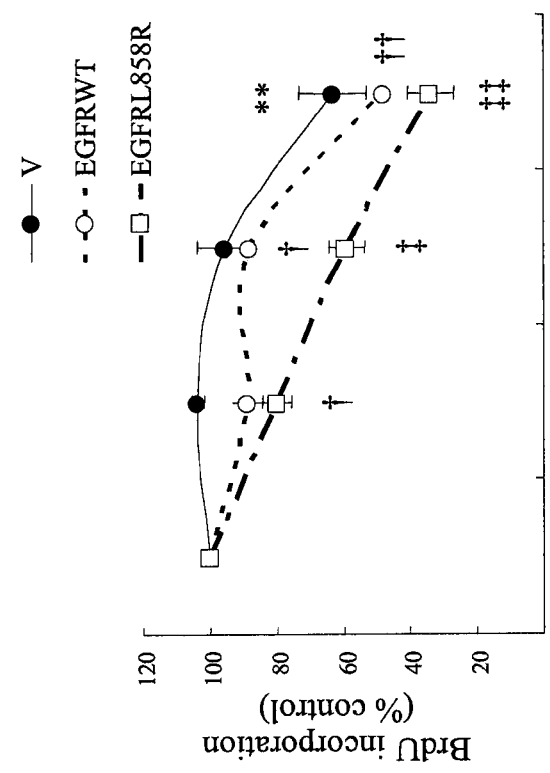

Gefitinib Induces Apoptosis and Suppresses Proliferation of Murine Corticotroph Adenoma Cells We tested effects of gefitinib on murine corticotroph adenoma cell proliferation. Gefitinib decreased EGFRWT and L858R but not V cell proliferation (~40%, p<0.01 in EGFRL858R, ~65%, p<0.01 in EGFR WT, FIG. 3A). Gefitinib also dose-dependently reduced formation of colonies by these transfectants in soft agar (~60%, p<0.01, FIG. 3B). TUNEL staining showed that inhibition of EGFR kinase also induced apoptosis (FIG. 3C), and western blot results showed elevated p53 and cleaved caspase3 levels (FIG. 3D). BrdU incorporation results showed that 1 μM gefitinib treatment reduced S phase entry in EGFR transfectants (~10%, p<0.05 in EGFR WT, ~40%, p<0.01 in EGFRL858R, FIG. 3E). Sensitivity to the drug was higher in EGFRL858R, which is the drug sensitive mutant prevalent in lung carcinoma[25,26]. Highest doses (10 μM) of drug reduced BrdU incorporation even in V only (~58%, p<0.01 in V, ~50%, p<0.01 in EGFRWT, ~70%, p<0.01 in EGFRL858R, FIG. 3E), while cell number was not altered with the high dose in V cells (FIG. 3A). We then analyzed effects of gefitinib on intracellular signaling molecules. Western blot results showed that gefitinib enhanced p27 expression (~1.4 fold, p<0.05), attenuated phospho-Rb (Ser780) (~44%, p<0.05), E2F1 (~50%, p<0.05), and PTTG levels (~18%, p<0.05) respectively (FIG. 3F).

Example 6

In Vivo Effects of Gefitinib on EGFR-Overexpressing AtT20 Allografts

Figure 4:
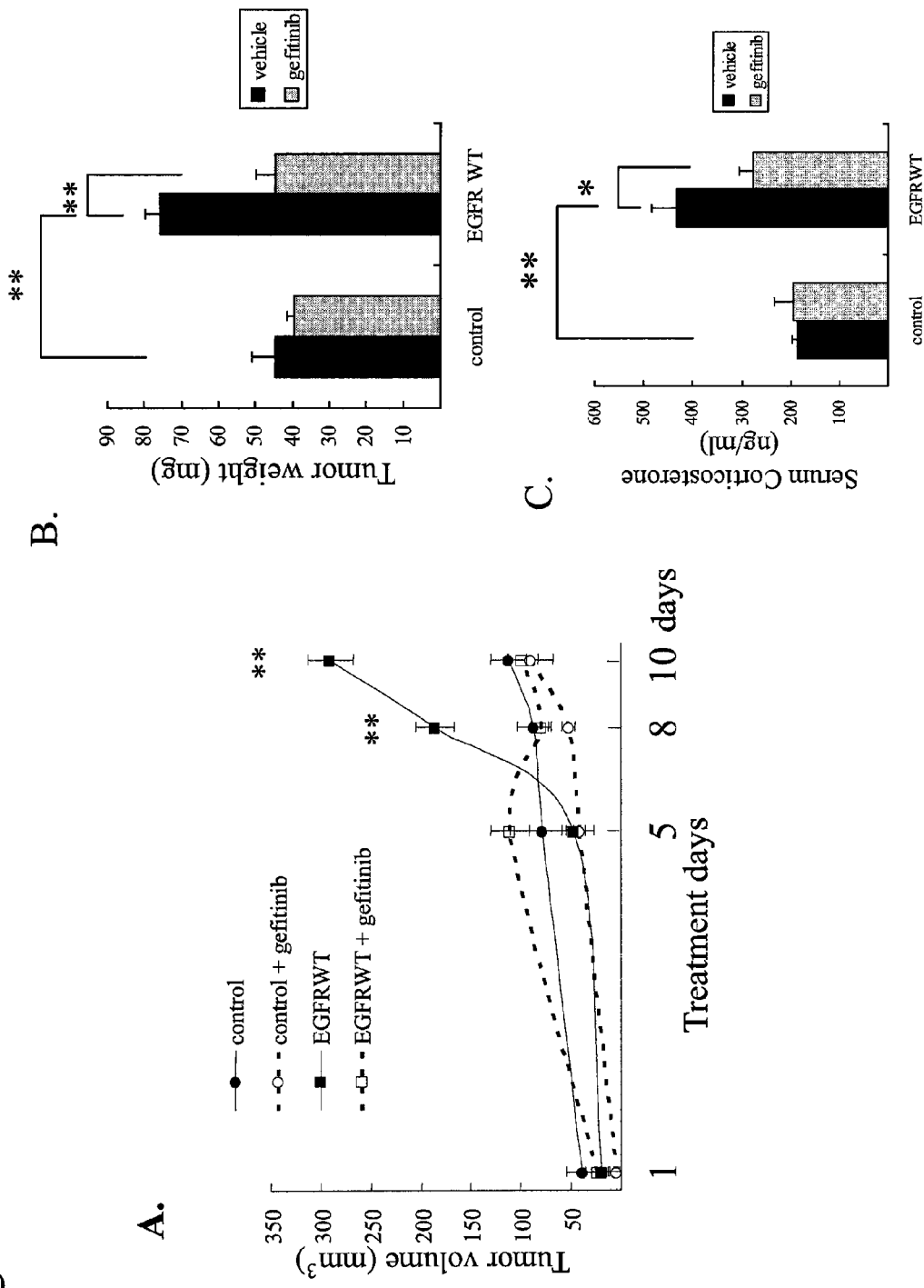
FIG. 4 shows that Gefitinib attenuates EGFRWT tumor growth and hormone secretion in vivo. EGFRWT ($1 \times 10^6$ cells/mouse, 0.1 ml with matrigel) or V transfectants were injected subcutaneously in nude mice (7 week of age). Three days after inoculation, mice with EGFRWT or V were divided into two groups respectively; vehicle (received 0.5% methylcellose, and 0.5% tween80/PBS), or gefitinib (received 100 mg/kg) for 10 days A. Tumor volume was measured by caliper and calculated using the formula, $\pi/6 \times \text{large diameter} \times \text{small diameter}^2$ at the indicated times after treatment. B. Excised tumors weighted after euthanasia. C. Serum corticosterone levels were measured by RIA. D. Omental fat was more prominent in mice injected with EGFRWT than control. Plasma glucose levels (E), and murine body weight (F) were measured after euthanasia. Values are mean±SEM. * $p<0.05$, ** $p<0.01$.
Figure 4:
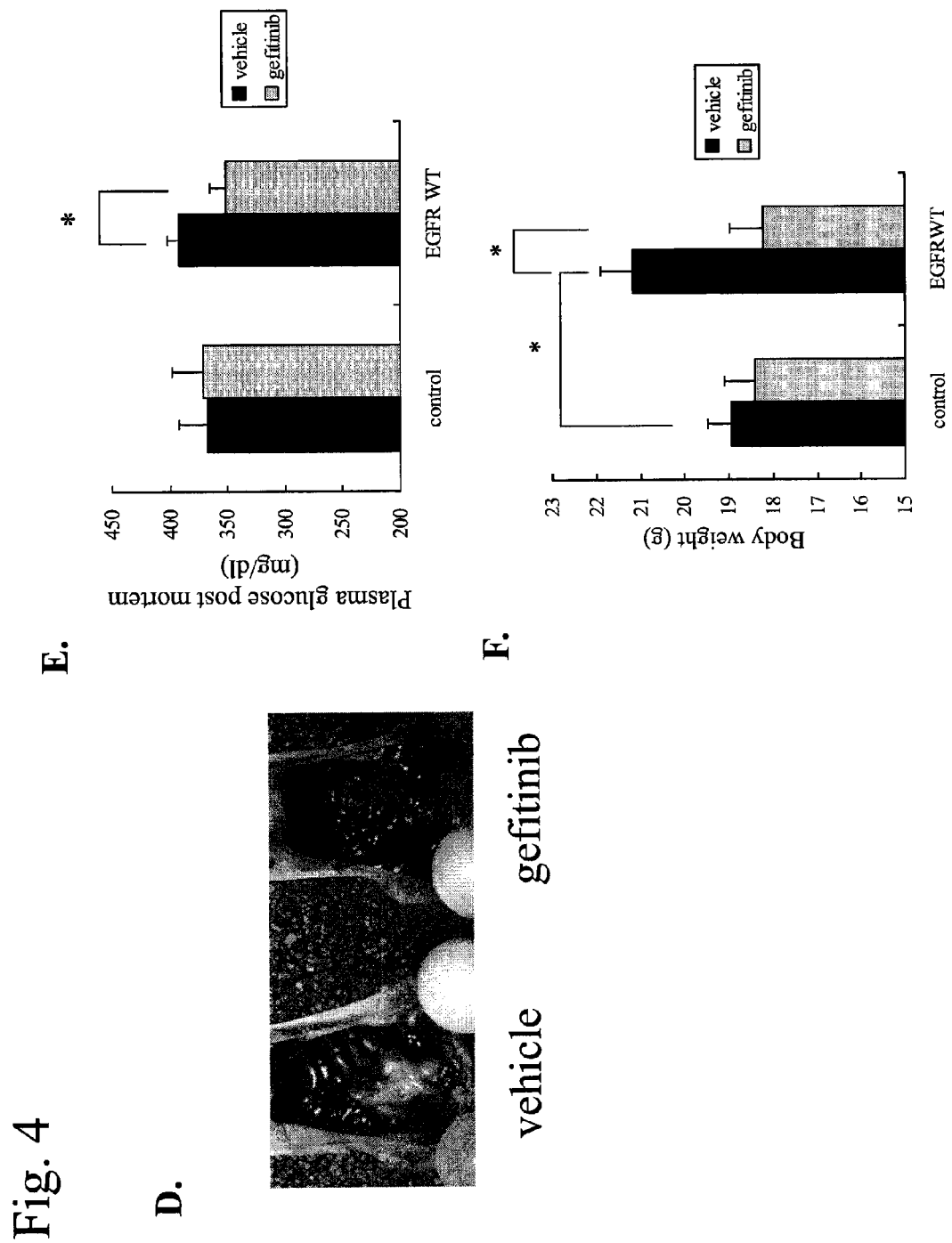

To evaluate effects of gefitinib in vivo, EGFRWT or control transfectants were inoculated subcutaneously into seven-week old female nude mice (NU/J), and animals randomized to receive either oral gefitinib (100 mg/kg/day) or vehicle. Drug treatment was started from three days after cell inoculation (1×10⁶ cells/mouse). As shown in FIGS. 4A and B, EGFRWT tumors thus generated were larger than controls (~3 fold, p<0.01), and gefitinib treatment significantly (~40%, p<0.01) inhibited tumor growth only in EGFR expressing tumors. Elevated serum corticosterone levels in the EGFRWT group (432±52 ng/ml vs 186±12 ng/ml, p<0.01) were attenuated by oral gefitinib treatment (~35%, p<0.05, FIG. 4C). Mice injected with EGFRWT transfectants showed fat accumulation, hyperglycemia and weight gain, all of which were attenuated by oral gefitinib treatment (FIGS. 4D, E and F). Notably, in mice injected with control AtT20 cells, which are devoided of EGFR serum corticosterone, fat accumulation, glucose levels and body weight were not altered by oral gefitinib treatment.

Example 7

Effects of Gefitinib on ACTH Producing Canine Pituitary Tumor Cells

Figure 5:
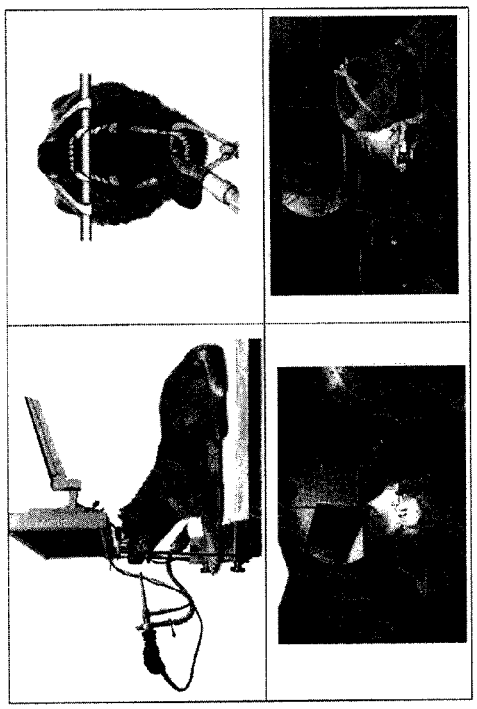
FIG. 5 shows that Gefitinib attenuates pomc mRNA expression and ACTH secretion in canine corticotroph adenoma cell cultures. A. shows establishment of modified trans-sphenoidal surgery for dog pituitary tumor B. After trans-sphenoidal surgery of canine ACTH-secreting adenomas, tumor cells were dispersed and cultured. Corticotroph adenoma cells were treated with gefitinib (0.1-10 µM) for 24 hours, and pomc expression levels measured by Real-time PCR. C. ACTH levels in culture media were measured using RIA. D. Confocal immunocytochemistry for ACTH, Tpit, and EGFR were performed in corticotroph tumors. Magnification of these figures was 100×. E. Taqman PCR was performed using specific canine egfr probe. Values are mean±SEM. * $p<0.05$,  $p<0.01$ vs. control. * $p<0.001$ vs. control. F. Gefitnib does not affect the normal pituitary. G. Confocal immunohistochemistry for ACTH, TPit and Her 2 were performed in corticotroph tumors.
Figure 5:
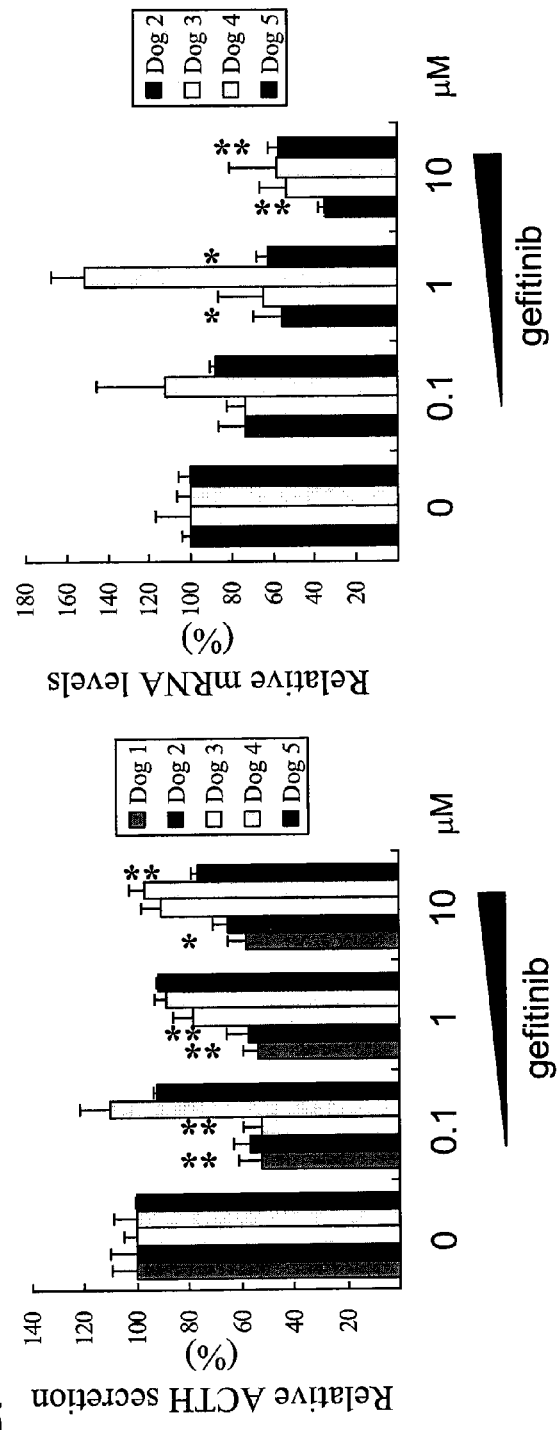
Figure 5:
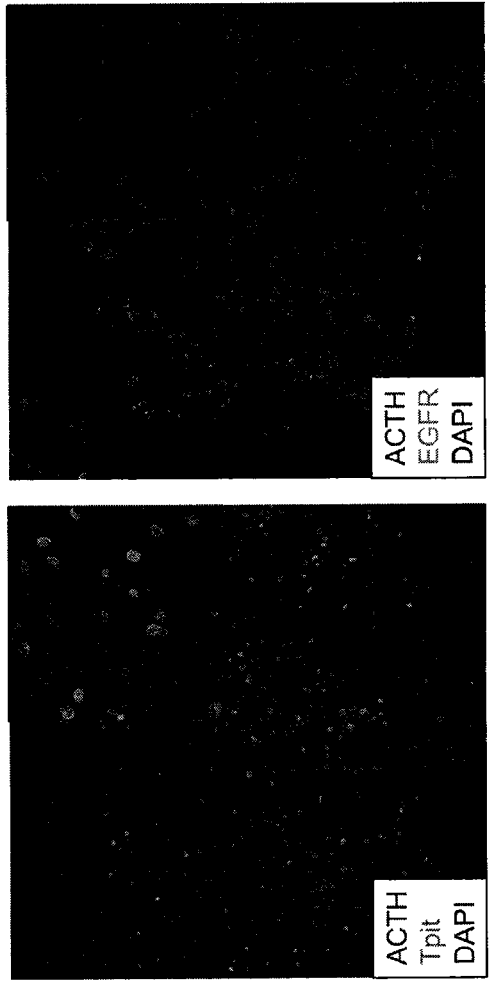
Figure 5:
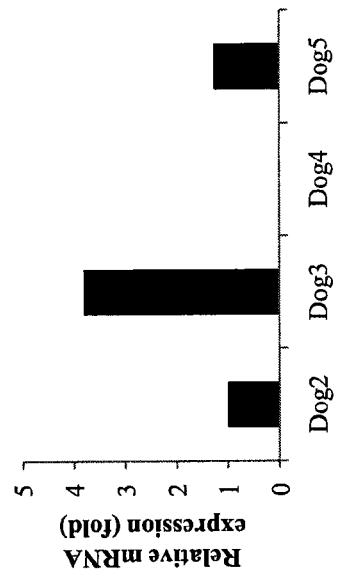
Figure 5:
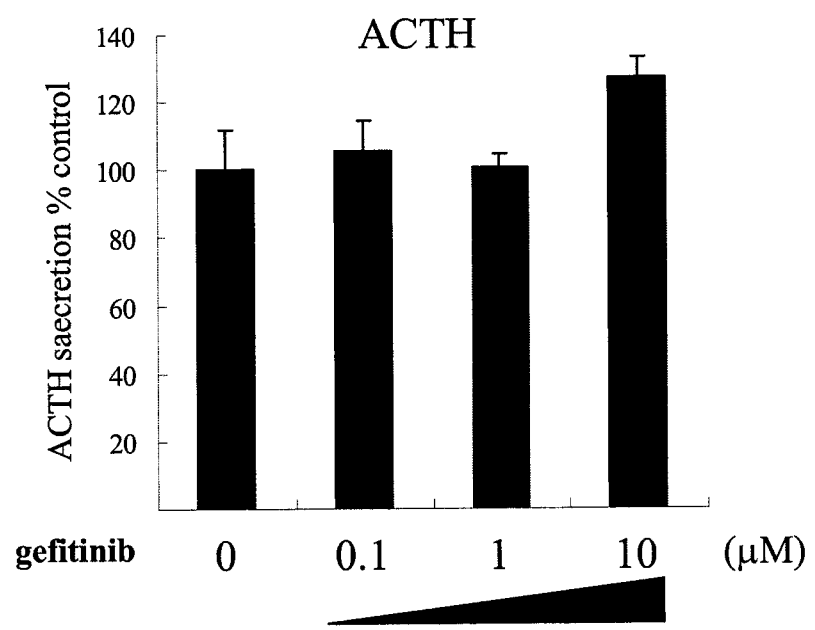
Figure 5:
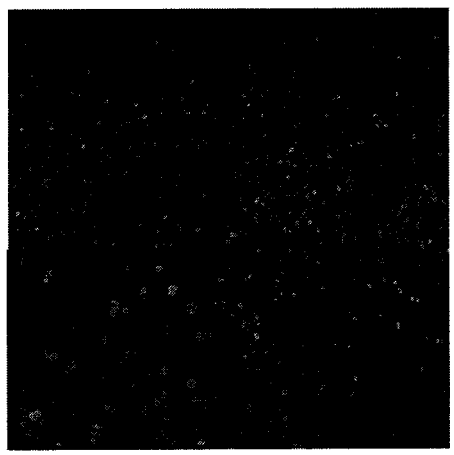
Figure 5:
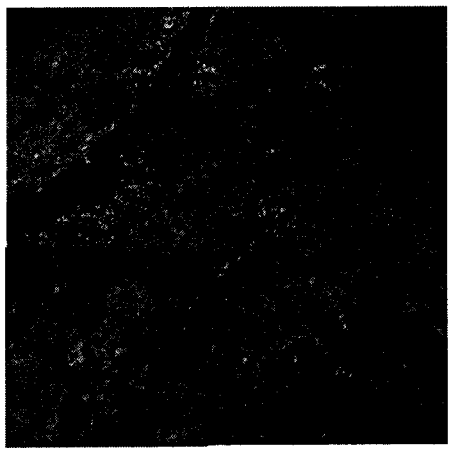
Figure 6:
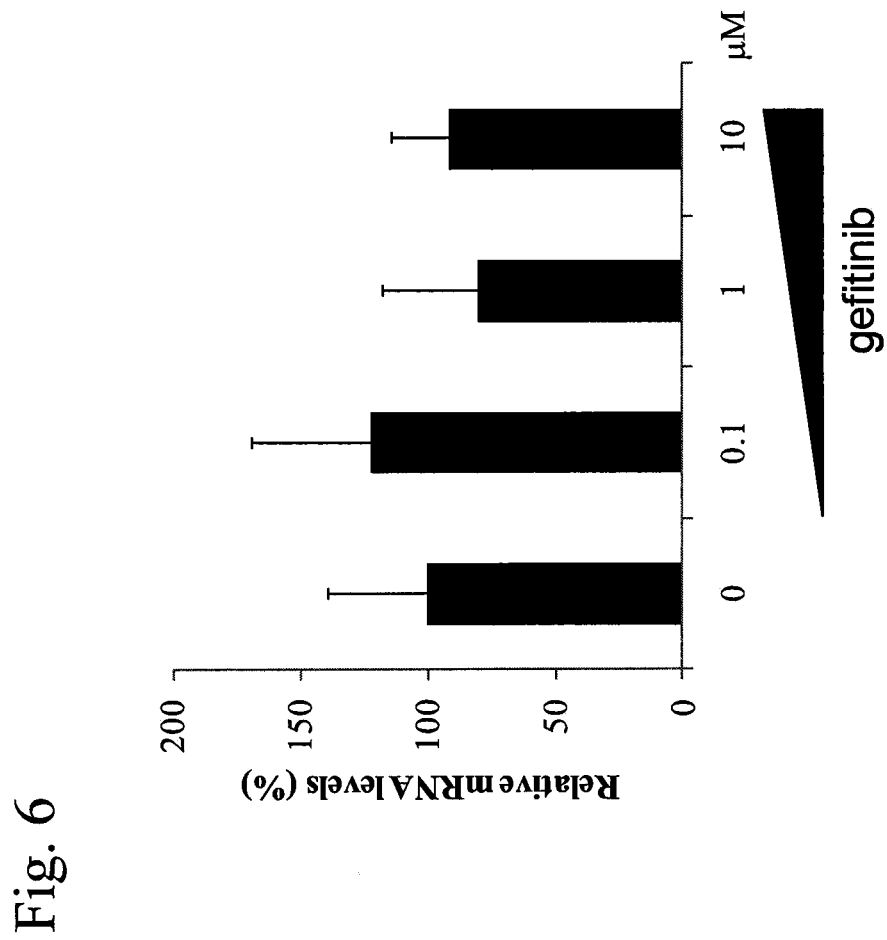
FIG. 6 shows that in non-tumor pituitary cell cultures, pomc mRNA expression levels were unaltered by gefitnib.

We have established an approach for transsphenoidal surgical removal of canine ACTH producing pituitary tumors by modifying the previously described trans-oral method[27] (FIG. 5A). To further investigate whether EGFR could be useful for targeting human ACTH producing pituitary tumors, we treated primary cell cultures derived from five surgically resected canine Cushing's tumors with gefitinib (0.1 to 10 μM) for 24 hours. Gefitnib does not affect normal pituitary function (FIG. 5F). In four of 5 tumor cell cultures, gefitinib suppressed pomc mRNA levels (~45%, p<0.01) and ACTH secretion to the media (~60%, p<0.01) (FIG. 5B, C). In non-tumor pituitary cell cultures, pomc mRNA expression levels were unaltered by gefitinib (FIG. 6). We confirmed ACTH and Tpit expression in these tumors using immunofluorescence, and also detected nuclear EGFR expression (FIG. 5D). To confirm canine tumor EGFR expression, we performed Taqman PCR using canine-specific EGFR probes, and showed that three of 4 tumors which responded to gefitinib expressed EGFR (FIG. 5D). These results suggest that ACTH suppression induced by gefitinib is mediated by EGFR expression.

Example 8

To investigate the role of EGFR in Cushing's disease, Applicants generated stably overexpressed EGFR in AtT20 murine corticotroph adenoma cells, which do not express EGFR endogenously[28]. Using these cells, we show that EGF enhances pomc expression and secretion in an EGFR dependent manner. Pomc expression is regulated by several transcriptional factors including Nur, STAT3, Neuro D1, Tpit, Pitx1, NF-κB, CREB, and GR[29-34]. To unravel mechanisms underlying EGF induction of pomc promoter activity, Applicants performed deletion analysis of the pomc promoter, and found the Pitx1 responsive element dependent transactivity by EGF.

Gefitinib also induced apoptosis and inhibited AtT20 cell proliferation. Antiproliferative and pro-apoptotic effects of gefitinib have been shown in several cancer cells, including non-small cell lung cancer (NSCLC) cells, breast and prostate cancer cells[26,35,36]. In NSCLC, a somatic mutation of EGFR (L858R) renders the tumors particularly sensitivity to gefitinib[25]. In the present study, antiproliferative and anti apoptotic effects of gefitinib were more marked in EGFRL858R than in EGFRWT transfectants. In human Cushing's tumors, mutations of EGFR have not been detected[16]. Gefitinib treatment also induced p27$^{kip1}$, a cyclin dependent kinase inhibitor shown to be down-regulated in Cushing's tumors[37,38].

Furthermore, mice lacking p27 developed pomc-expressing pituitary tumors suggesting a requirement for p27 in corticotroph cell tumorigenesis[17]. Taken together, these results support the role of EGFR in pathogenesis of Cushing's adenomas.

Using immunofluorescence, Applicants detected nuclear EGFR expression in both canine and human Cushing's tumors. Nuclear EGFR localization has been reported in breast, ovarian, and thyroid cancers[39-41], likely due to ligand-dependent EGFR nuclear translocation[42]. Nuclear EGFR may act as a transcription factor[43] and directly induce proliferating cell nuclear antigen (PCNA) phosphorylation[44]. Nuclear EGFR has also been shown to confer drug resistance to cetuximab, a monoclonal antibody for EGFR[45]. However, Applicants reported the efficacy of tyrosine kinase inhibitors for prolactinomas, which also expressed nuclear EGFR[13].

Gefitinib effectively suppressed ACTH secretion and inhibited tumor growth in EGFR expressing tumors in vivo, supporting our in vitro results. In mice injected with EGFRWT transfectants, attenuating effects of gefitinib on feature of hypercortisolism including fat accumulation, plasma glucose levels, and body weight, were paralleled by reductions in serum corticosterone, indicating that effects of gefitinib are mediated by its tumoral hormone suppression.

Canine pituitary-dependent hyperadrenocorticism (PDH), synonymous with Cushing's disease in humans, is common in dogs, and the clinical signs are similar to the human disease, including central obesity, ravenous appetite, polyuria, polydipsia, a "pot belly" appearance, thin skin, and loss of hair[46]. Using primary cell cultures derived from surgically resected canine corticotroph adenomas, we show inhibition of EGFR kinase activity on pomc expression and ACTH secretion. A single drug resistant tumor, which did not express EGFR, suggested that the hormone suppressive effects of gefitinib are mediated by EGFR.

EGFR-mediated induction of pomc transactivation is mediated by PitxRE in ACTH-secreting tumor cells. Blocking receptor tyrosine activity with gefitinib resulted in both in vivo and in vitro ACTH suppression, indicating that EGFR could be an molecular target for treating patients with Cushing's disease.

REFERENCES

1. Melmed, S. Mechanisms for pituitary tumorigenesis: the plastic pituitary. *The Journal of clinical investigation* 112, 1603-1618 (2003).
2. Biller, B. M., et al. Treatment of adrenocorticotropin-dependent Cushing's syndrome: a consensus statement. *The Journal of clinical endocrinology and metabolism* 93, 2454-2462 (2008).
3. Newell-Price, J., Trainer, P., Besser, M. & Grossman, A. The diagnosis and differential diagnosis of Cushing's syndrome and pseudo-Cushing's states. *Endocr Rev* 19, 647-672 (1998).
4. Boscaro, M., Barzon, L., Fallo, F. & Sonino, N. Cushing's syndrome. *Lancet* 357, 783-791 (2001).
5. Dwyer, A. J., et al. Pituitary adenomas in patients with Cushing disease: initial experience with Gd-DTPA-enhanced MR imaging. *Radiology* 163, 421-426 (1987).
6. Oldfield, E. H., et al. Petrosal sinus sampling with and without corticotropin-releasing hormone for the differential diagnosis of Cushing's syndrome. *The New England journal of medicine* 325, 897-905 (1991).
7. Patronas, N., et al. Spoiled gradient recalled acquisition in the steady state technique is superior to conventional post-contrast spin echo technique for magnetic resonance imaging detection of adrenocorticotropin-secreting pituitary tumors. *The Journal of clinical endocrinology and metabolism* 88, 1565-1569 (2003).
8. Boscaro, M., et al. Treatment of pituitary-dependent Cushing's disease with the multireceptor ligand somatostatin analog pasireotide (SOM230): a multicenter, phase II trial. *The Journal of clinical endocrinology and metabolism* 94, 115-122 (2009).
9. Pivonello, R., et al. The medical treatment of Cushing's disease: effectiveness of chronic treatment with the dopamine agonist cabergoline in patients unsuccessfully treated by surgery. *The Journal of clinical endocrinology and metabolism* 94, 223-230 (2009).
10. Melmed, S. Acromegaly pathogenesis and treatment. *The Journal of clinical investigation* 119, 3189-3202 (2009).
11. Herbst, R. S. Review of epidermal growth factor receptor biology. *Int J Radiat Oncol Biol Phys* 59, 21-26 (2004).
12. Childs, G. V., Rougeau, D. & Unabia, G. Corticotropin-releasing hormone and epidermal growth factor: mitogens for anterior pituitary corticotropes. *Endocrinology* 136, 1595-1602 (1995).
13. Fukuoka, H., et al. HER2/ErbB2 Receptor Signaling in Rat and Human Prolactinoma Cells: Strategy for Targeted Prolactinoma Therapy. *Mol Endocrinol* (2010).
14. Onguru, O., et al. Analysis of epidermal growth factor receptor and activated epidermal growth factor receptor expression in pituitary adenomas and carcinomas. *Mod Pathol* 17, 772-780 (2004).
15. LeRiche, V. K., Asa, S. L. & Ezzat, S. Epidermal growth factor and its receptor (EGF-R) in human pituitary adenomas: EGF-R correlates with tumor aggressiveness. *The Journal of clinical endocrinology and metabolism* 81, 656-662 (1996).
16. Theodoropoulou, M., et al. Expression of epidermal growth factor receptor in neoplastic pituitary cells: evidence for a role in corticotropinoma cells. *The Journal of endocrinology* 183, 385-394 (2004).
17. Kiyokawa, H., et al. Enhanced growth of mice lacking the cyclin-dependent kinase inhibitor function of p27(Kip1). *Cell* 85, 721-732 (1996).
18. Nakayama, K., et al. Mice lacking p27(Kip1) display increased body size, multiple organ hyperplasia, retinal dysplasia, and pituitary tumors. *Cell* 85, 707-720 (1996).
19. Fero, M. L., et al. A syndrome of multiorgan hyperplasia with features of gigantism, tumorigenesis, and female sterility in p27(Kip1)-deficient mice. *Cell* 85, 733-744 (1996).
20. Roussel-Gervais, A., et al. Cooperation between cyclin E and p27(Kip1) in pituitary tumorigenesis. *Mol Endocrinol* 24, 1835-1845 (2010).
21. Wang, Q. & Greene, M. I. Mechanisms of resistance to ErbB-targeted cancer therapeutics. *The Journal of clinical investigation* 118, 2389-2392 (2008).
22. Mok, T. S., et al. Gefitinib or carboplatin-paclitaxel in pulmonary adenocarcinoma. *The New England journal of medicine* 361, 947-957 (2009).
23. Mellinghoff, I. K., et al. Molecular determinants of the response of glioblastomas to EGFR kinase inhibitors. *The New England journal of medicine* 353, 2012-2024 (2005).

24. Cohen, E. E., et al. Phase II trial of gefitinib 250 mg daily in patients with recurrent and/or metastatic squamous cell carcinoma of the head and neck. *Clin Cancer Res* 11, 8418-8424 (2005).

25. Paez, J. G., et al. EGFR mutations in lung cancer: correlation with clinical response to gefitinib therapy. *Science* 304, 1497-1500 (2004).

26. Tracy, S., et al. Gefitinib induces apoptosis in the EGFRL858R non-small-cell lung cancer cell line H3255. *Cancer Res* 64, 7241-7244 (2004).

27. Meij, B. P. Hypophysectomy as a treatment for canine and feline Cushing's disease. *Vet Clin North Am Small Anim Pract* 31, 1015-1041 (2001).

28. Vlotides, G., et al. Rat prolactinoma cell growth regulation by epidermal growth factor receptor ligands. *Cancer Res* 68, 6377-6386 (2008).

29. Kovalovsky, D., et al. Activation and induction of NUR77/NURR1 in corticotrophs by CRH/cAMP: involvement of calcium, protein kinase A, and MAPK pathways. *Mol Endocrinol* 16, 1638-1651 (2002).

30. Bousquet, C., Zatelli, M. C. & Melmed, S. Direct regulation of pituitary proopiomelanocortin by STAT3 provides a novel mechanism for immuno-neuroendocrine interfacing. *The Journal of clinical investigation* 106, 1417-1425 (2000).

31. Jenks, B. G. Regulation of proopiomelanocortin gene expression: an overview of the signaling cascades, transcription factors, and responsive elements involved. *Ann N Y Acad Sci* 1163, 17-30 (2009).

32. Poulin, G., Turgeon, B. & Drouin, J. NeuroD1/beta2 contributes to cell-specific transcription of the proopiomelanocortin gene. *Mol Cell Biol* 17, 6673-6682 (1997).

33. Lamolet, B., et al. A pituitary cell-restricted T box factor, Tpit, activates POMC transcription in cooperation with Pitx homeoproteins. *Cell* 104, 849-859 (2001).

34. Karalis, K. P., Venihaki, M., Zhao, J., van Vlerken, L. E. & Chandras, C. NF-kappaB participates in the corticotropin-releasing, hormone-induced regulation of the pituitary proopiomelanocortin gene. *J Biol Chem* 279, 10837-10840 (2004).

35. Moon, D. O., et al. Gefitinib induces apoptosis and decreases telomerase activity in MDA-MB-231 human breast cancer cells. *Arch Pharm Res* 32, 1351-1360 (2009).

36. Festuccia, C., et al. Molecular aspects of gefitinib antiproliferative and pro-apoptotic effects in PTEN-positive and PTEN-negative prostate cancer cell lines. *Endocrine-related cancer* 12, 983-998 (2005).

37. Lidhar, K., et al. Low expression of the cell cycle inhibitor p27Kip1 in normal corticotroph cells, corticotroph tumors, and malignant pituitary tumors. *The Journal of clinical endocrinology and metabolism* 84, 3823-3830 (1999).

38. Bamberger, C. M., et al. Reduced expression levels of the cell-cycle inhibitor p27Kip1 in human pituitary adenomas. *Eur J Endocrinol* 140, 250-255 (1999).

39. Lo, H. W., et al. Novel prognostic value of nuclear epidermal growth factor receptor in breast cancer. *Cancer Res* 65, 338-348 (2005).

40. Marti, U., et al. Nuclear localization of epidermal growth factor and epidermal growth factor receptors in human thyroid tissues. *Thyroid* 11, 137-145 (2001).

41. Xia, W., et al. Nuclear expression of epidermal growth factor receptor is a novel prognostic value in patients with ovarian cancer. *Mol Carcinog* 48, 610-617 (2009).

42. Lo, H. W., et al. Nuclear interaction of EGFR and STAT3 in the activation of the iNOS/NO pathway. *Cancer Cell* 7, 575-589 (2005).

43. Lin, S. Y., et al. Nuclear localization of EGF receptor and its potential new role as a transcription factor. *Nat Cell Biol* 3, 802-808 (2001).

44. Wang, S. C., et al. Tyrosine phosphorylation controls PCNA function through protein stability. *Nat Cell Biol* 8, 1359-1368 (2006).

45. Li, C., Iida, M., Dunn, E. F., Ghia, A. J. & Wheeler, D. L. Nuclear EGFR contributes to acquired resistance to cetuximab. *Oncogene* 28, 3801-3813 (2009).

46. Kemppainen, R. J. & M, E. P. Animal models of Cushing's disease. *Trends Endocrinol Metab* 5, 21-28 (1994).

47. Chesnokova, V., Auernhammer, C. J. & Melmed, S. Murine leukemia inhibitory factor gene disruption attenuates the hypothalamo-pituitary-adrenal axis stress response. *Endocrinology* 139, 2209-2216 (1998).

48. Ben-Shlomo, A., et al. Constitutive somatostatin receptor activity determines tonic pituitary cell response. *Mol Endocrinol* 23, 337-348 (2009).

49. Ben-Shlomo, A., et al. Leukemia inhibitory factor regulates prolactin secretion in prolactinoma and lactotroph cells. *The Journal of clinical endocrinology and metabolism* 88, 858-863 (2003).

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method for treating Cushing's Disease and/or hypercortisolism in a subject in need thereof, comprising:
   (i) providing a composition comprising gefitinib; and
   (ii) administering a therapeutically effective amount of the composition to the subject to treat Cushing's Disease and/or hypercortisolism, thereby treating Cushing's Disease and/or hypercortisolism in the subject.

2. A method for inhibiting Cushing's Disease and/or hypercortisolism in a subject in need thereof, comprising:
   (i) providing a composition comprising gefitinib; and
   (ii) administering a therapeutically effective amount of the composition to the subject to inhibit Cushing's Disease and/or hypercortisolism, thereby inhibiting Cushing's Disease and/or hypercortisolism in the subject.

3. A method for reducing size of tumor associated with Cushing's Disease and/or hypercortisolism in a subject in need thereof comprising:
   (i) providing a composition comprising gefitinib; and
   (ii) administering a therapeutically effective amount of the composition to the subject to reduce the Cushing's Disease and/or hypercortisolism, thereby reducing the Cushing's Disease and/or hypercortisolism tumor size in the subject.

4. A method for promoting Cushing's Disease and/or hypercortisolism prophylaxis in a subject in need thereof comprising:
   (i) providing a composition comprising gefitinib; and
   (ii) administering a therapeutically effective amount of the composition to the subject to promote Cushing's Disease and/or hypercortisolism prophylaxis, thereby promoting Cushing's Disease and/or hypercortisolism prophylaxis in the subject.

5. The method of claim 1, wherein gefitinib is administered intravenously, intramuscularly, intraperitonealy, orally or via inhalation.

6. A method of claim 1, wherein the effective amount of gefitinib is about 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day or 1900-2000 mg/day.

7. The method of claim 1, wherein the subject is selected from the group consisting of human, non-human primate, monkey, ape, dog, cat, cow, horse, rabbit, mouse and rat.

* * * * *

SEQUENCE LISTING

<160> NUMBER OF SEQ ID NOS: 16

<210> SEQ ID NO 1
<211> LENGTH: 35
<212> TYPE: DNA
<213> ORGANISM: Artificial Sequence
<220> FEATURE:
<223> OTHER INFORMATION: Synthetic

<400> SEQUENCE: 1
cgagtcgacg atcttgattt cacaagactc catac                    35

<210> SEQ ID NO 2
<211> LENGTH: 29
<212> TYPE: DNA
<213> ORGANISM: Artificial Sequence
<220> FEATURE:
<223> OTHER INFORMATION: Synthetic

<400> SEQUENCE: 2
cgtgtcgacg gcagatggac gcacacagg                           29

<210> SEQ ID NO 3
<211> LENGTH: 28
<212> TYPE: DNA
<213> ORGANISM: Artificial Sequence
<220> FEATURE:
<223> OTHER INFORMATION: Synthetic

<400> SEQUENCE: 3
agagtcgacc ctgcctcaca ccaggatg                            28

<210> SEQ ID NO 4
<211> LENGTH: 27
<212> TYPE: DNA
<213> ORGANISM: Artificial Sequence
<220> FEATURE:
<223> OTHER INFORMATION: Synthetic

<400> SEQUENCE: 4
gtggtcgacc cagcctccgc actttcc                             27

<210> SEQ ID NO 5
<211> LENGTH: 25
<212> TYPE: DNA
<213> ORGANISM: Artificial Sequence
<220> FEATURE:
<223> OTHER INFORMATION: Synthetic

<400> SEQUENCE: 5
cgcgtcgacg accgggaagc ccccc                               25

<210> SEQ ID NO 6
<211> LENGTH: 30
<212> TYPE: DNA
<213> ORGANISM: Artificial Sequence
<220> FEATURE:
<223> OTHER INFORMATION: Synthetic

<400> SEQUENCE: 6
gccgtcgact cgcttgttgc gttgcagaag                          30

<210> SEQ ID NO 7
<211> LENGTH: 31
<212> TYPE: DNA
<213> ORGANISM: Artificial Sequence -continued
<220> FEATURE:
<223> OTHER INFORMATION: Synthetic

<400> SEQUENCE: 7
cagggatcct gttcagtggc ctctcttagt c          31

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
ggacatctaa gggcatcaca                       20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tcaagaacga aagtcggagg                       20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ggcctctgtg gaagtgagtg                       20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
acgccagcag gttactttcc                       20

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
cctcctgccg tattaccctt g                     21

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
tctggacgaa gtaacccttg g                     21

```
<210> SEQ ID NO 14
<211> LENGTH: 19
<212> TYPE: DNA
<213> ORGANISM: Artificial Sequence
<220> FEATURE:
<223> OTHER INFORMATION: Synthetic

<400> SEQUENCE: 14
tcactggtga gaaccccct                                                    19

<210> SEQ ID NO 15
<211> LENGTH: 19
<212> TYPE: DNA
<213> ORGANISM: Artificial Sequence
<220> FEATURE:
<223> OTHER INFORMATION: Synthetic

<400> SEQUENCE: 15
cctgattcac acggcgtag                                                    19

<210> SEQ ID NO 16
<211> LENGTH: 36
<212> TYPE: DNA
<213> ORGANISM: Artificial Sequence
<220> FEATURE:
<223> OTHER INFORMATION: Synthetic

<400> SEQUENCE: 16
caagtcgaca ggtataaaag aagagagaag agtgac                                 36
```